(12) United States Patent
Tsumuraya et al.

(10) Patent No.: US 8,208,600 B2
(45) Date of Patent: Jun. 26, 2012

(54) X-RAY GENERATING APPARATUS AND X-RAY CT APPARATUS USING THE SAME

(75) Inventors: Yoshiaki Tsumuraya, Tokyo (JP); Hironori Ueki, Tokyo (JP); Keiji Koyanagi, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

(21) Appl. No.: 12/669,556

(22) PCT Filed: Jul. 18, 2008

(86) PCT No.: PCT/JP2008/063015
§ 371 (c)(1),
(2), (4) Date: Jan. 18, 2010

(87) PCT Pub. No.: WO2009/011422
PCT Pub. Date: Jan. 22, 2009

(65) Prior Publication Data
US 2010/0183117 A1 Jul. 22, 2010

(30) Foreign Application Priority Data
Jul. 19, 2007 (JP) .................. 2007-187863

(51) Int. Cl.
*G01N 23/00* (2006.01)
(52) U.S. Cl. ............................... 378/9; 378/4
(58) Field of Classification Search ............ 378/4–20, 378/124
See application file for complete search history.

(56) References Cited

U.S. PATENT DOCUMENTS

| 2003/0210764 A1* | 11/2003 | Tekletsadik et al. ......... 378/106 |
| 2004/0247082 A1* | 12/2004 | Hoffman ....................... 378/119 |
| 2005/0100132 A1 | 5/2005 | Block et al. |
| 2006/0115050 A1* | 6/2006 | Resnick ......................... 378/108 |
| 2007/0086571 A1 | 4/2007 | Hempel et al. |
| 2010/0080357 A1* | 4/2010 | Katcha et al. ................ 378/124 |

FOREIGN PATENT DOCUMENTS

| JP | 63-49142 | 3/1988 |
| JP | 2000-79111 | 3/2000 |
| JP | 2005-142160 | 6/2005 |
| JP | 2007-95689 | 4/2007 |
| JP | 2007-165081 | 6/2007 |

* cited by examiner

*Primary Examiner* — Hoon Song
(74) *Attorney, Agent, or Firm* — Cooper & Dunham LLP

(57) ABSTRACT

There are provided an X-ray generating apparatus capable of switching X-ray beams of high energy and low energy to each other at high speed, and an X-ray CT apparatus capable of performing high-speed and high-quality multi-energy imaging by using the same. The X-ray generating apparatus is constructed by an X-ray tube 9 having two anodes 200a, 200b, a rotational anode 204 for radiating X-ray from an X-ray focal point by electron beams emitted from filaments of these cathodes, and two grid electrodes 202a and 202b for controlling emission of the electron beams, a tube voltage generator 9a and a tube voltage controller 9d1 for controlling an X-ray condition, a filament heater 9b and a tube current controller 9d2, a grid voltage generator 9c and a grid opening/closing controller 9d3, and a grid switching unit 9e. High energy X-ray and low energy X-ray are switched and emitted to an examinee every adjacent projection angles, thereby collecting projection data.

14 Claims, 18 Drawing Sheets

X-RAY GENERATING APPARATUS AND X-RAY CT APPARATUS USING THE SAME

TECHNICAL FIELD

The present invention relates to an X-ray generating apparatus, and particularly to an X-ray generating apparatus suitable for multi-energy imaging, and an X-ray CT apparatus having a function of performing multi-energy imaging by using the X-ray generating apparatus.

BACKGROUND ART

As X-ray CT apparatuses are known a single slice type X-ray CT apparatus for obtaining one tomogram by one X-ray exposure and a multi-slice type X-ray CT apparatus for simultaneously obtaining plural tomograms by one X-ray exposure.

According to the single slice type X-ray apparatus, an X-ray detector having many X-ray detection elements arranged on a line, that is, in a one-dimensional direction (channel direction) is used, a fan beam, that is, a sectorial X-ray beam is emitted from an X-ray tube to an examinee and X-ray which has passed through the examinee is measured to obtain projection data of the examinee.

On the other hand, according to the multi-slice type X-ray CT apparatus, a cone beam, that is, a conical or pyramidal X-ray beam is emitted from an X-ray tube to an examinee, and X-ray which has passed through the examinee is measured by an X-ray detector having many X-ray detection elements arranged in a two-dimensional direction (channel direction and line direction), thereby obtaining projection data.

In both the X-ray CT apparatuses, the X-ray tube and the X-ray detector which are opposed to each other are rotated around the examinee to collect projection data in many directions, and these collected projection data are subjected reconstructing filtering processing for correction of blurring, and then the data are inversely projected to reconstruct a tomogram(s) of the examinee.

The projection data is collected at a discrete projection angle (hereinafter referred to as "view") of an X-ray beam emitted from the X-ray tube, and the thus-collected projection data is referred to as "the projection data at the corresponding view"). The number of views per rotation of the X-ray tube and the X-ray detector rotating around the examinee, which is required to reconstruct one CT image, normally ranges from several hundreds to about one thousand. Furthermore, the projection data of one view comprises data corresponding to the number of channels×the number of lines of the X-ray detector (in the case of the single slice type X-ray CT apparatus, the number of lines=1 as described above).

Recently, a method of analyzing the composition of an examinee on the basis of images picked up by irradiating the same cross-sectional plane with X-ray beams having plural different energies has been used in the X-ray CT apparatuses as described above, and this method is called as a multi-energy imaging method.

Particularly, when imaging is performed by using two different kinds of energies, it is called as a dual energy imaging method.

A method of measuring tomograms of an average atomic number and an average density of an examinee by applying the dual energy imaging method is disclosed in Non-patent Document 1.

Furthermore, a method of performing the dual energy imaging while the voltage between the anode and the cathode of the X-ray tube (hereinafter referred to as "tube voltage") is varied every X-ray projection angle to change the energy spectrum of the X-ray (hereinafter referred to as "tube voltage modulation method") is disclosed in Patent Document 1.

Non-patent Document 1: R. E. Alvarez and A. Macovski, "Energy-selective Reconstructions in X-ray Computed Tomography," Phys. Med. Biol. Vol. 21, No. 5, pp. 733-744, (1976)

Patent Document 1: JP-A-10-73544

In order to pick up an image of a fast-moving site of an examinee such as a heart, coronary artery or the like, it has been proposed to increase the rotating speed (that is, the scan speed of an imaging system comprising a pair of an X-ray tube and an X-ray detector), in an X-ray CT apparatus for medical application, and X-ray CT apparatuses of about 0.33 to 0.4 [second/revolution] have been practically used.

In such X-ray CT apparatus whose scan speed is increased, the number of views per rotation of the imaging system in normal X-ray CT imaging is equal to about 1,000, and when the scan speed is equal to 0.33 second, imaging is once carried out per rotation of 0.36° (=360°/1,000).

On the other hand, when dual energy imaging is applied to the conventional X-ray CT apparatus as described above by using the technique of the patent document 1, the following problems occur.

(1) Current flowing between the anode and the cathode of the X-ray tube (hereinafter referred to as "tube current") is fixed irrespective of the magnitude of the tube voltage.

This is because it is difficult to switch the tube current at high speed due to thermal inertia of the filament temperature of the X-ray tube and thus the tube current is controlled to be fixed at a high energy (high tube voltage) and at a low energy (low tube voltage), so that the tube current is not switched.

Normally, the X-ray amount absorbed in an examinee increases when imaging is carried out at a low tube voltage, and thus the tube current is required to be larger than that at the high tube voltage.

Furthermore, when the tube current runs short at the low tube voltage, the quantum noise in the pickup image increases, and the quality of the pickup image is lowered.

Still furthermore, it is possible to obtain sufficient projection data at the high tube voltage, and thus it is desired that the tube current is set to be less than that at the low tube voltage from the viewpoint of reduction of exposure.

For the foregoing reason, it is originally desired to vary the tube current (reduce the tube current/increase the tube current) in connection with the variation of the tube voltage.

(2) In the technique described in the patent document 1, as described in paragraph number [0058] of the patent document 1, the number of views which are obtained in each of the high energy case and the low energy case during one rotation of a scanner is equal to 600 and this is a small number. Accordingly, when each view data obtained in each of the high energy case and the low energy case is subjected to image reconstruction, there is concern about occurrence of a radial artifact.

This is because a delay occurs in a process of supplying the tube voltage from a power source portion to the X-ray tube due to parasitic impedance (parasitic inductance and parasitic electrostatic capacitance) possessed by wires and thus increase of the switching speed of the tube voltage is restricted, thereby limiting the number of views.

SUMMARY

In an aspect of this disclosure, there is provided an X-ray generating apparatus that can switch X-ray beams of high energy and low energy to each other at high speed in multi-energy imaging using a tube voltage modulation method, and an X-ray CT apparatus that can obtain a multi-energy pickup image having high image quality at high speed by using the X-ray generating apparatus.

In another aspect, there is provided an X-ray generating apparatus comprising an X-ray tube for generating and alternately switching X-rays having different energies based on electron beams generated from plural cathodes by opening and closing grids, and X-ray control means for controlling the X-rays having the different energies. The X-rays having the different energies are emitted while alternatively switched to each other every adjacent views, thereby obtaining projection data in the X-ray generating apparatus, and an image is reconstructed from the projection data concerned. Specifically, the X-ray generating apparatus is implemented by the following means.

In an X-ray generating apparatus including an X-ray tube for emitting X-ray, tube current control means for controlling tube current of the X-ray tube, and X-ray control means for controlling high-energy X-ray and low-energy X-ray by the tube voltage control means, according to another aspect, the X-ray tube has plural cathodes each of which has a filament, an anode opposed to the plural cathodes, and grid electrodes each of which is individually provided every cathode to control discharge of an electron beam emitted from the cathode, and comprises grid voltage generating means for generating a voltage to be applied to each grid electrode, and electron beam emission control means for alternately applying the grid voltage generated in the grid voltage generating means to each of the grid electrodes to control the emission of the electron beam.

The X-ray tube may be an X-ray tube for emitting plural electron beams from the plural filaments and forming plural X-ray focal points on the anode so that the X-ray focal points are spaced from one another at a predetermined distance on the anode. Furthermore, the X-ray tube may be an X-ray tube having electron beam deflecting means which has a deflection coil provided between the anode and the plural cathodes and deflection current supply means for supplying the deflection coil with current for deflecting the directions of the electron beams and deflects the directions of the electron beams generated from the plural filaments.

The tube voltage control means has first tube voltage control means for controlling a high tube voltage corresponding to the high energy X-ray, and second tube voltage control means for controlling a low tube voltage corresponding to the low energy X-ray, and the tube current control means has first tube current control means for controlling tube current corresponding to the high energy X-ray, and second tube current control means for controlling tube current corresponding to the low energy X-ray.

The tube current controlled by the second tube current control means is larger than the tube current controlled by the first tube current control means.

In an X-ray CT apparatus that has a multi-energy imaging function, uses the aforementioned X-ray generating apparatus and comprises an X-ray tube for irradiating X-ray with an examinee, an X-ray detector for detecting X-ray transmitted through the examinee, scanner rotating means rotating around the examinee while the X-ray tube and the X-ray detector are mounted therein, X-ray control means for irradiating X-rays having plural different energies emitted from the X-ray tube to the same slice position of the examinee while switching the X-rays every projection angle, and image reconstructing means for reconstructing projection data detected by the X-ray detector to obtain a CT image, according to another aspect, the X-ray tube comprises plural cathodes each of which has a filament, an anode opposed to the plural cathodes, and grid electrodes each of which is individually provided every cathode to control emission of an electron beam emitted from the cathode, and the X-ray control means comprises tube current control means for heating the cathode filaments of the X-ray tube and control the tube current flowing between the anode and the cathodes, tube voltage control means for controlling a tube voltage to be applied between the anode and the cathodes, grid voltage generating means for generating a voltage to be applied to each grid electrode, and electron beam emission control means for applying the grid voltages generated in the grid voltage generating means to the respective grid electrodes while alternately switching the grid voltages every projection angle, thereby controlling emission of the electron beams.

The X-ray tube of the X-ray CT apparatus may be an X-ray tube for emitting plural electron beams from the plural filaments and forming plural X-ray focal points on the anode so that the X-ray focal points are spaced from each other at a predetermined distance. Furthermore, the X-ray tube may be an X-ray tube having electron beam deflecting means that has a deflection coil provided between the anode and the plural cathodes and deflection current supply means for supplying the deflection coil with current for deflecting the directions of the electron beams, and deflects the directions of the electron beams generated from the plural filaments.

The tube voltage control means of the X-ray CT apparatus has first tube voltage control means for controlling a high tube voltage corresponding to the high energy X-ray, and second tube voltage control means for controlling a low tube voltage corresponding to the low energy X-ray, and the tube current control means has first tube current control means for controlling tube current corresponding to the high energy X-ray, and second tube current control means for controlling tube current corresponding to the low energy X-ray.

The tube current controlled by the second tube current control means is increased to be larger than the tube current controlled by the first tube current control means, whereby the image quality is enhanced by reduction of exposure and reduction of quantum noise.

The number of projection angles for detecting the projection data is set to be larger than that under normal CT imaging, thereby setting the image quality of the normal CT image to the same level as prior arts.

Thus, an X-ray generating apparatus can be provided that uses the X-ray tube having the plural cathodes, the anode for forming the X-ray focal points by electron beams emitted from the filaments of the plural cathodes and the plural grid electrodes corresponding to the plural cathode to control the emission of the plural electron beams, and controls the voltage applied to the grid electrodes so that the high-energy X-ray and the low-energy X-ray can be switched to each other at high speed.

In the aforementioned X-ray generating apparatus, the high energy X-ray and the low energy X-ray are alternately switched and emitted every adjacent views to obtain projection data. Therefore, the number of views can be set to the double number of that under normal CT imaging, and no radial artifact occurs. Therefore, the enhancement of the image quality can be performed, and issues of a human body can be clearly discriminated.

Further, when high-energy X-ray is generated by a high tube voltage, the tube current is reduced from the viewpoint of reduction of exposure, and when low energy X-ray is generated by a low tube voltage, X-ray is generated while the tube current is increased to the extent that the quantum noise in the image is not increased. Therefore, both the enhancement of the image quality and the reduction of the exposure can be attained.

Figure 1:
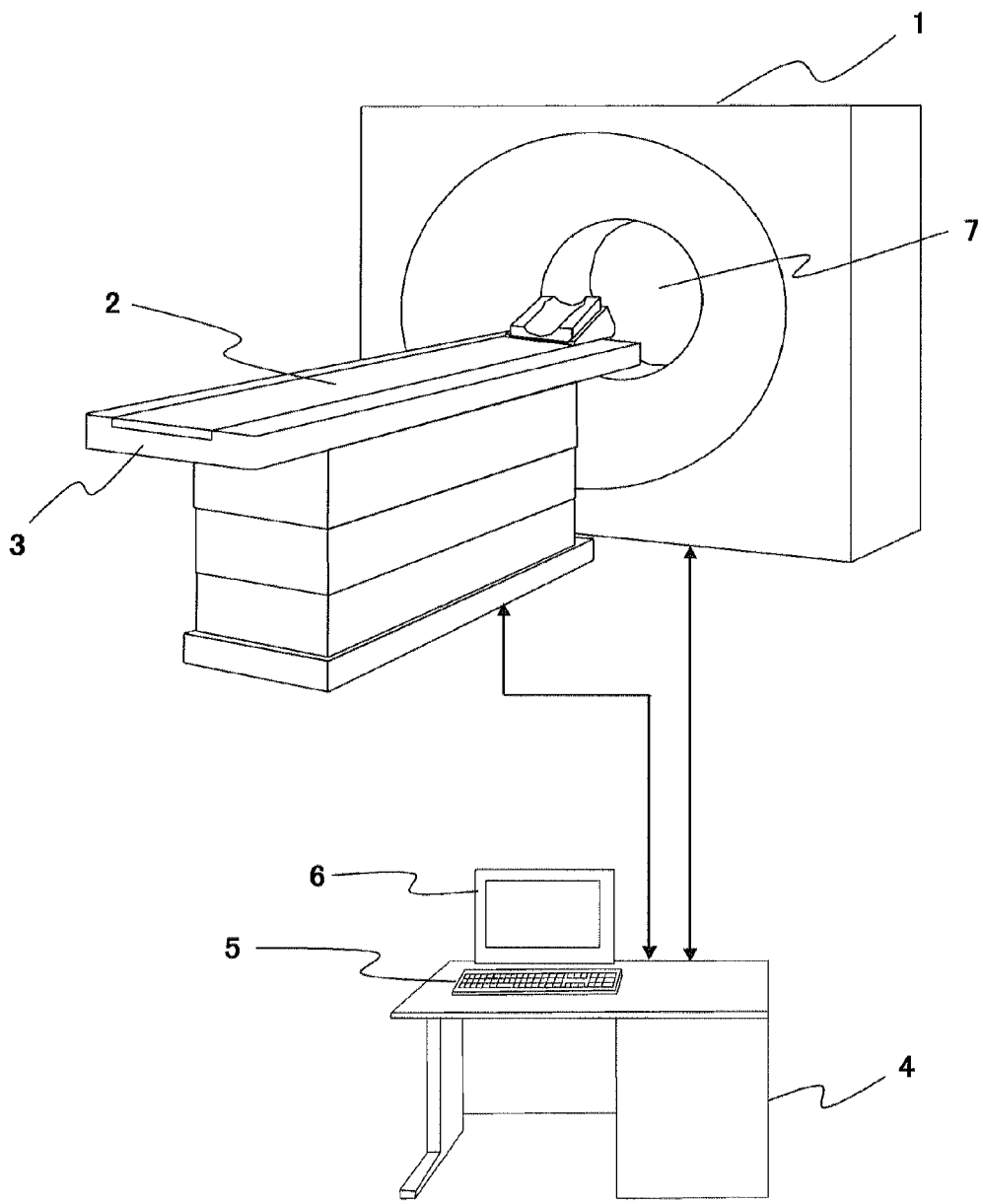
FIG. 1 is a schematic diagram showing an X-ray CT apparatus to which the present invention is applied.

DESCRIPTION OF REFERENCE NUMERALS 1 scanner gantry, 4 operation console, 5 operation device, 6 display device, 8 X-ray control device, 9 X-ray tube, 9a tube voltage generator, 9b filament heater, 9c grid voltage generator, 9d controller, 9d1 tube voltage controller, 9d2 tube current controller, 9d3 grid opening/closing controller, 9e grid switching unit, 12 X-ray detecting device, 15 data collecting device, 16 scanner rotating plate, 20 system control device, 21 image processing device, 21a frame memory, 21b projection data adder, 21c image reconstructing unit, 21d data converter, 21e material identifier, 200a first cathode, 200b second cathode, 201a first grid electrode, 201b second grid electrode, 202a first electron beam, 202b second electron beam, 203 X-ray focal point, 204 rotational anode, 300 X-ray focal point position on scanner rotating plate, 600 deflection coil, 701 outer envelope of X-ray tube, 702 filament, 702a first filament, 702b second filament, β distance between cathode and anode, θ angle of cathode opposed to anode

BEST MODES FOR CARRYING OUT THE INVENTION

Preferred embodiments of an X-ray generating apparatus and an X-ray CT apparatus for performing multi-energy imaging by using the X-ray generating apparatus according to the invention will be described in detail with reference to the accompanying drawings.

<<First Embodiment>>

Figure 2:
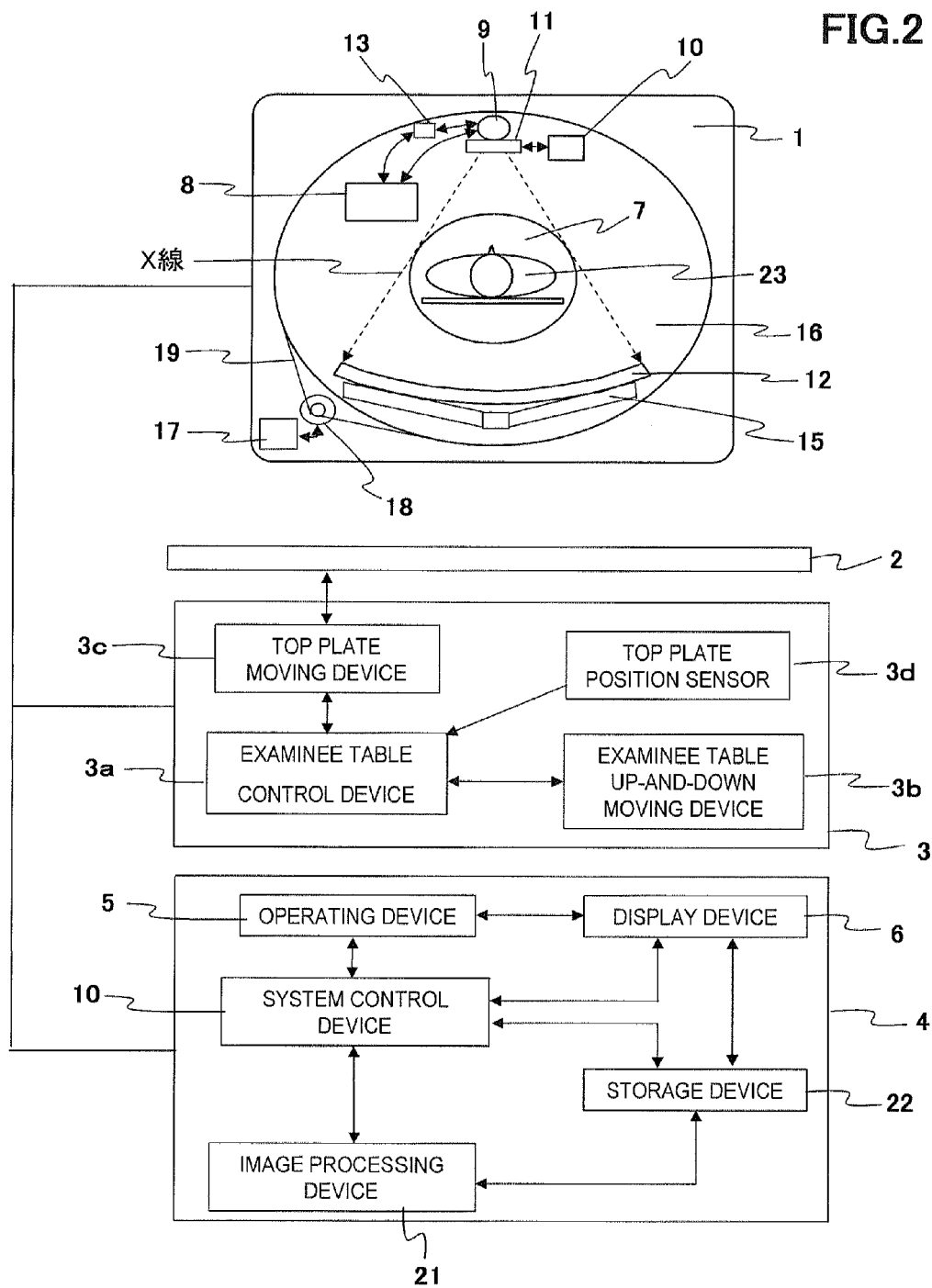
FIG. 2 is a diagram showing the overall construction of the X-ray CT apparatus to which the present invention is applied.

FIG. 1 is a diagram showing the construction of an X-ray CT apparatus to which the present invention is applied, and FIG. 2 is a block diagram showing the overall construction of the X-ray CT apparatus. The X-ray CT apparatus shown in FIG. 1 irradiates an examinee with X-ray to collect transmitted X-ray data of the examinee, and subjects the collected X-ray data to reconstructing calculation to obtain a tomogram, and it is constructed by a scanner gantry 1, a table 3 having a top plate 2 on which the examinee is mounted, and an operation console 4.

An opening portion 7 in which the examinee is inserted is provided at the center portion of the scanner gantry 1, and the table 3 is disposed at the front side of the gantry 1.

The height of the table 3 can be adjusted by electric operation, and the top plate 2 is provided on the upper surface of the table 3. The top plate 2 is constructed to be slidable with respect to the gantry 1 by electric operation in order to position the examinee to an imaging position.

An operation device 5 such as a keyboard, a mouse, etc., and a display device 6 for displaying various kinds of information such as patient information, imaging conditions, etc. and a pickup tomogram are disposed on the operation console 4. An image processing device described later and a system control device (CPU) for controlling the overall system are mounted in the operation console 4. The gantry 1 and the table 3 are controlled by the system control device (CPU).

As shown in FIG. 2, the scanner gantry 1 has an X-ray tube 9 which is controlled by the X-ray control device 8 to generate X-ray, a collimator 11 for narrowing down X-ray emitted from the X-ray tube 9 to a predetermined irradiation field and an X-ray detector 12. The X-ray emitted from the X-ray tube 9 is shaped to a pyramidal X-ray beam, that is, a cone beam by the collimator 11 which is controlled by the collimator control device 10, and applied to the examinee 23. The X-ray transmitted through the examinee 23 is incident to the X-ray detector 12.

The X-ray control device 8 controls the tube voltage and the tube current so that the tube voltage and the tube current become the tube voltage and the tube current corresponding to a scan condition set by the operation device 5. Therefore, a tube voltage/tube current detecting device 13 for detecting the tube voltage applied between the anode and cathode of the X-ray tube 9 and the current flowing between the anode and cathode of the X-ray tube 9 is provided.

Figure 3:
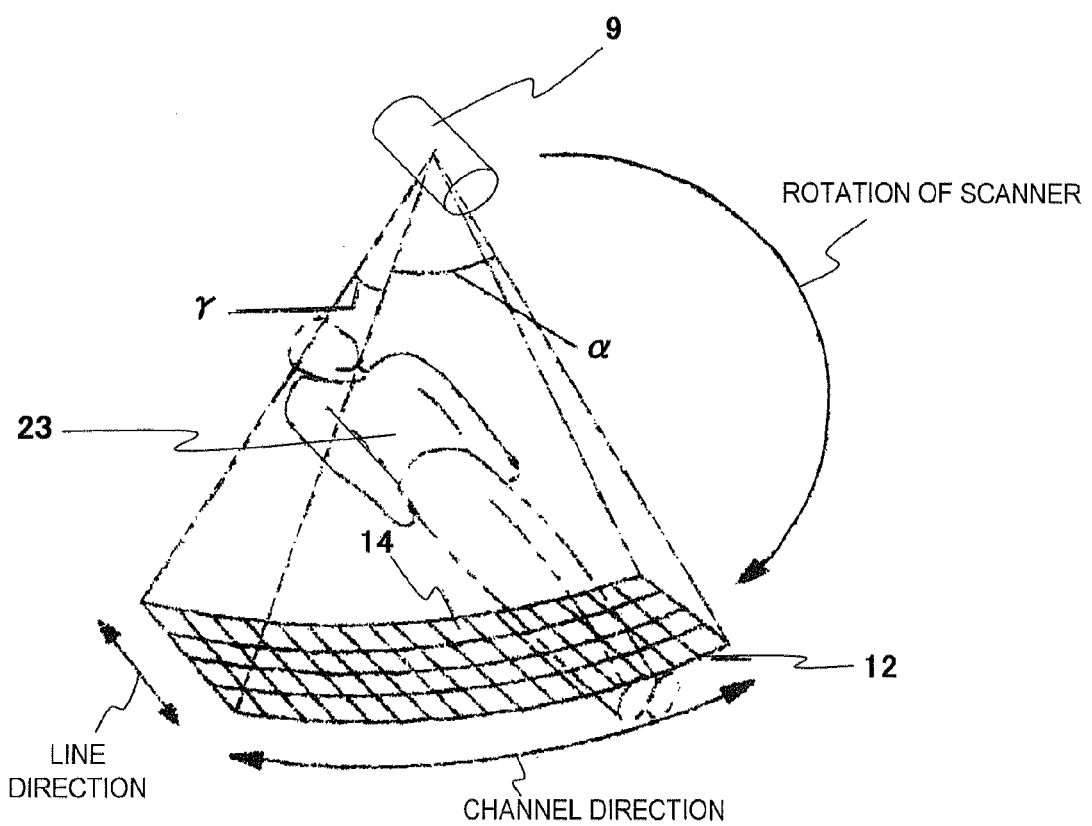
FIG. 3 is a diagram showing the relation between X-ray irradiation and the construction of an X-ray detector of the X-ray CT apparatus to which the present invention and X-ray irradiation.

The X-ray detector 12 has plural X-ray detecting elements 14 arranged two-dimensionally in a channel direction and a line direction as shown in FIG. 3.

This X-ray detector 14 is constructed by the combination of a scintillator and a photodiode, for example, and it constitutes an X-ray incident face which is designed in a cylindrical plane shape as a whole or curved like a broken line with respect to the channel direction. The single slice type X-ray detector is not excluded from this invention.

Here, a spread angle of the cone beam X-ray in the channel direction, that is, a fan angle is represented by $\alpha$, and a spread angle in the line direction, that is, a cone angle is represented by $\gamma$.

A data collecting device 15 is connected to the thus-constructed X-ray detector 12, and the data collecting device 15 collects detection data of the X-ray detecting elements 14 constituting the X-ray detector 12.

The constituent elements from the X-ray control device 8 till the data collecting device 15 are mounted on a rotational plate 16 (scanner rotating means) of the scanner gantry 1. Driving force from a rotational plate driving device 18 controlled by a rotation control device 17 is transmitted by a driving force transmission system 19, whereby the rotational plate 16 rotates round the examinee 23.

The examinee table 3 has an examinee table control device 3a, an examinee table up-and-down moving device 3b and a top plate moving device 3c. The examinee table control device 3a controls the examinee table up-and-down moving device 3b so as to set the height of the table to a proper height, and also controls the top plate moving device 3c to move the top plate 2 in front-and-rear direction so that the examinee 23 is fed into and from the X-ray irradiation space (opening portion) of the scanner gantry 1. A top plate position sensor 3d detects the top plate position in the body axial direction and the vertical direction, and controls the top plate moving device 3c and the examinee table up-and-down moving device 3b on the basis of the detection information so that the examinee table control device 3a is set to a correct top plate position.

In the thus-constructed scanner gantry 1, when the examinee 23 mounted on the top plate 2 of the examinee table 3 is fed into the opening portion 7 of the scanner gantry 1 and then the examinee 23 is irradiated with a cone beam X-ray whose cone angle $\gamma$ is adjusted by the opening width of the collimator 11, an X-ray image of the examinee 23 irradiated with the cone beam X-ray is projected onto the X-ray detector 12, and X-ray transmitted through the examinee 23 is detected by the X-ray detector 12.

The operation console 4 has a system control device (CPU) 20 for controlling the overall CT system having a multi-energy imaging function of the X-ray CT apparatus according to this invention, and the scanner gantry 1 and the examinee table 3 are connected to the system control device (CPU) 20. That is, the X-ray control device 8, the collimator control device 10, the data collecting device 15 and the rotation control device 17 in the scanner gantry 1 and the examinee table control device 3a in the examinee table 3 are controlled by the system control device (CPU) 20.

The transmitted X-ray detection data collected by the data collecting device 15 is taken into the image processing device 21 under the control of the system control device (CPU) 20.

This image processing device 21 conducts various kinds of correction processing on the detection data of plural views collected by the data collecting device 15 to generate projection data, and performs CT image reconstruction by using this projection data.

A scanogram image required for set a scan condition, various kinds of data, programs for implementing the function of the X-ray CT apparatus, etc. are stored in a storage device 22 connected to the system control device (CPU) 20. The CT image reconstructed in the image processing device 21 is also stored in the storage device 22. Furthermore, the operation device 5 and the display device 6 are connected to the system control device (CPU) 20.

The operation device 5 is used by an operator to input various kinds of instructions and information, an image reconstruction mode, etc. into the system control device (CPU) 20, and interactively operate the X-ray CT apparatus by using the display device 6.

The display device 6 displays the reconstructed image output from the image processing device 21 and various kinds of information to be treated by the system control device (CPU) 20.

The system control device (CPU) 20 predetermines the scan condition by using an operation instruction input with the operator operating the operation device 5 and the scanogram image read out from the storage device 22 before scan is started. That is, the scanogram image read out from the storage device 22 is displayed on the display device 6, and the operator indicates the coordinate of a CT image reconstruction position (hereinafter referred to as slice position) on the displayed examinee scanogram image by using the operation device 5, whereby the slice position can be set. There is a case where the slice position is set by using no scanogram image. The slice position information set here is stored in the storage device 22, and also used to set an X-ray condition (tube voltage, tube current).

Power to the respective elements mounted in the thus-constructed gantry 1 is supplied from a commercial alternating power source by power transmitting means comprising a brush fixed to a fixed portion of the scanner gantry 1 (not shown) and a slipping brush provided to a rotating portion (rotational plate 16) of the scanner gantry 1, and transmission of the transmitted X-pray detection data collected by the data collecting device 15 to the image processing device 21 is performed by the same slipping mechanism as described above or optical signal transmitting means.

According to this invention, high energy X-ray and low energy X-ray from the X-ray tube 9 are alternately switched to each other every projection angle (view) to perform dual energy imaging by the thus-constructed X-ray CT apparatus. The X-ray tube shown in FIG. 4 is used in the first embodiment of the present invention.

Figure 4:
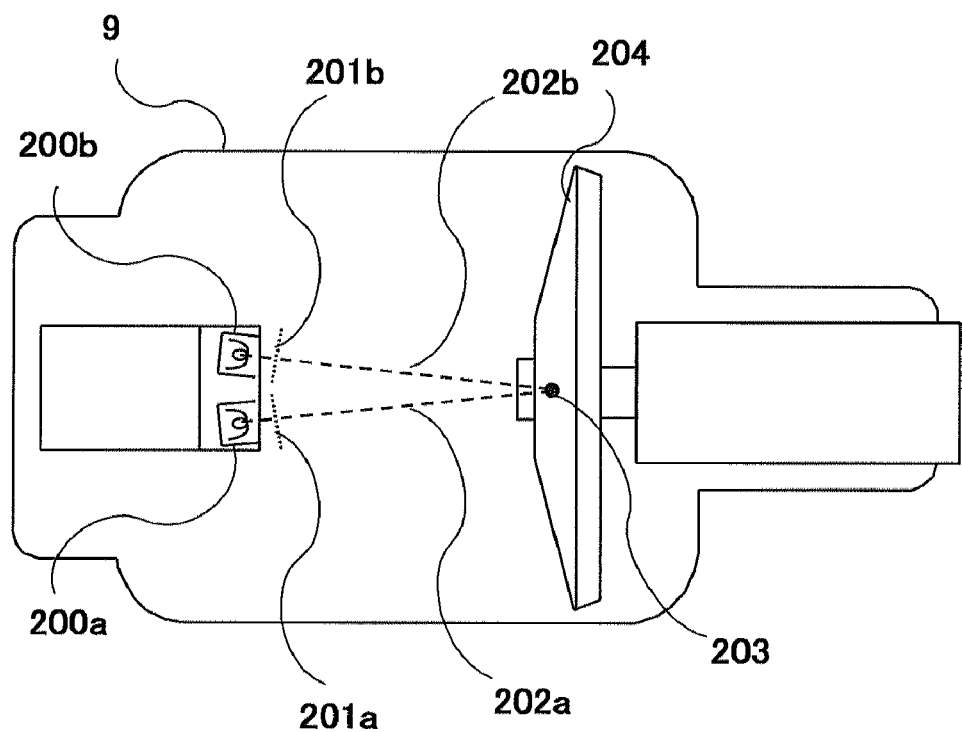
FIG. 4 is a diagram showing the construction of an X-ray tube used in a first embodiment of the present invention.

In FIG. 4, the X-ray tube 9 has a first cathode 200a for generating an electron beam 202a for generating the high energy X-ray, a second cathode 200b for generating an electron beam 202b for generating the low energy X-ray, a first grid 201a corresponding to the first cathode 200a and a second grid 201b corresponding to the second cathode 200b which are used to alternately switch the electron beam 202a and the electrode beam 202b to each other, and a rotational anode 204 on which the electron beams 202a and 202b emitted from the cathodes 200a and 200b are focused to form the same focal points 203. The focal points 203 are formed at the same position by adjusting the distance between the cathode 200a,200b and the rotational anode 204 and the angle of the anode 200a, 200b opposed to the anode 204.

Figure 5:
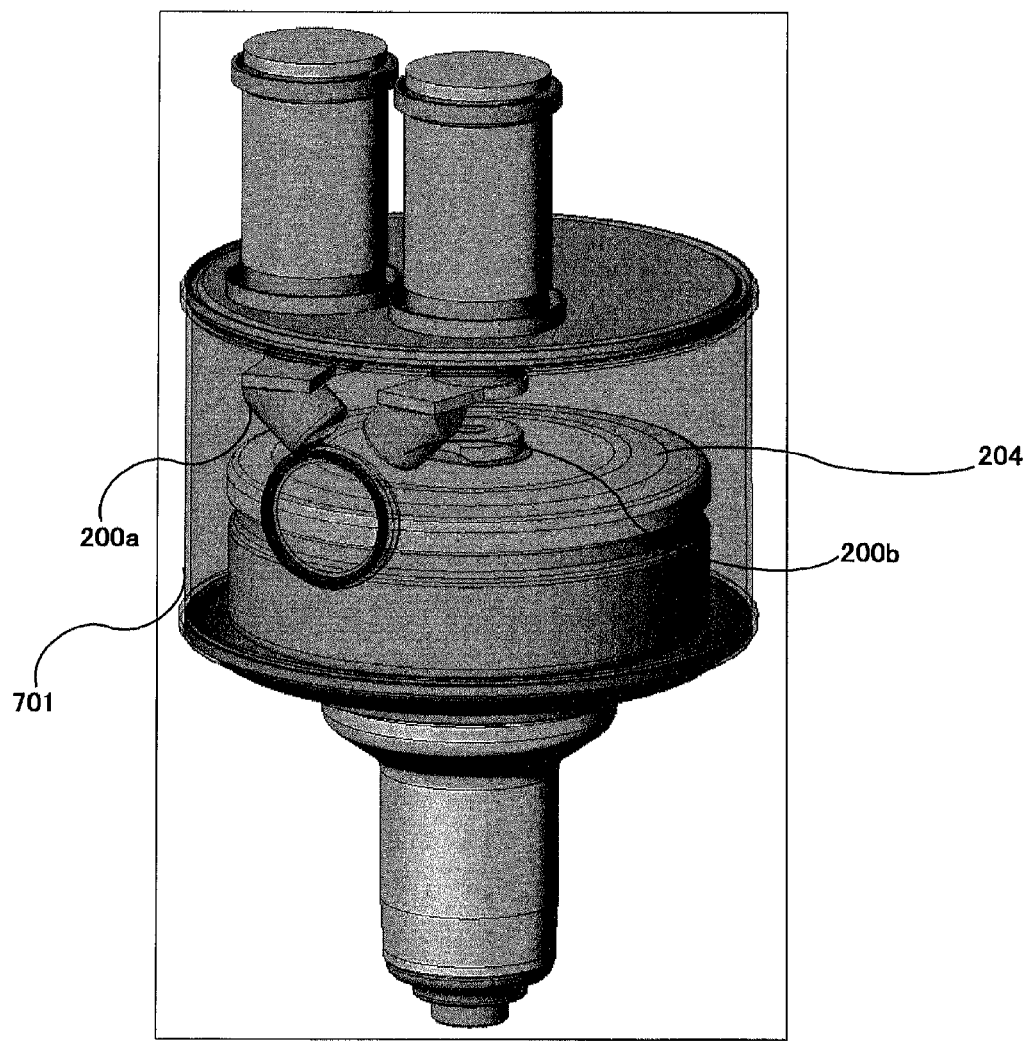
FIG. 5 is a diagram showing the structure of the X-ray tube used in the first embodiment of the present invention.
Figure 6:
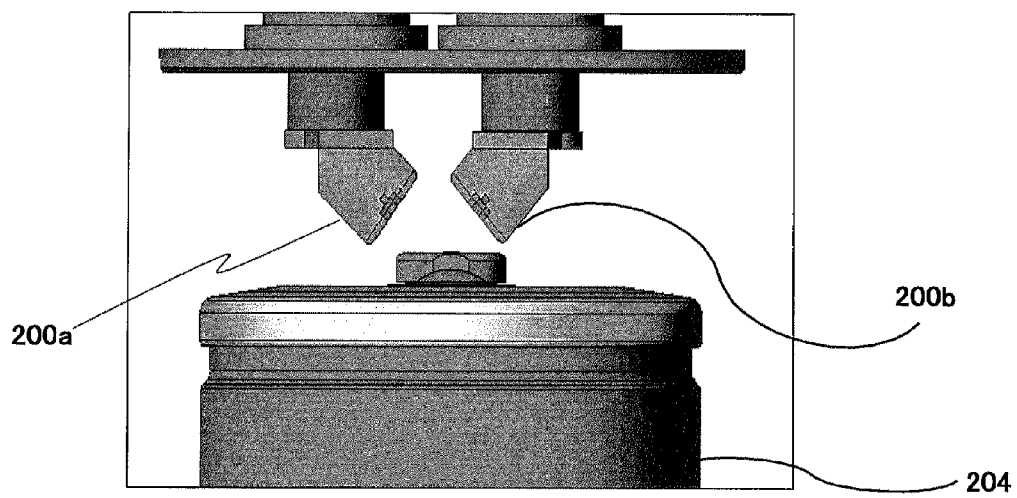
FIG. 6 is an enlarged view of the neighborhood of a cathode of the X-ray embodiment used in the first embodiment of the present invention.
Figure 7:
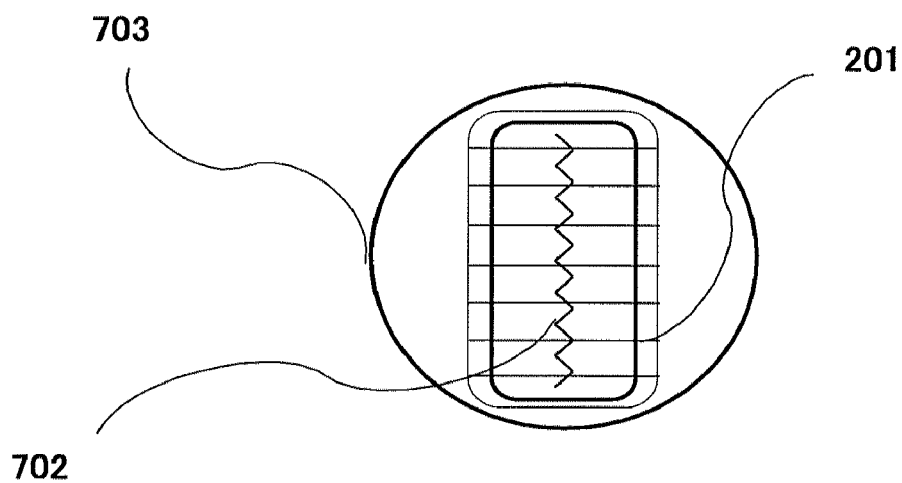
FIG. 7 is a diagram showing the detailed construction of the cathode of the X-ray tube used in the first embodiment of the present invention.
Figure 8:
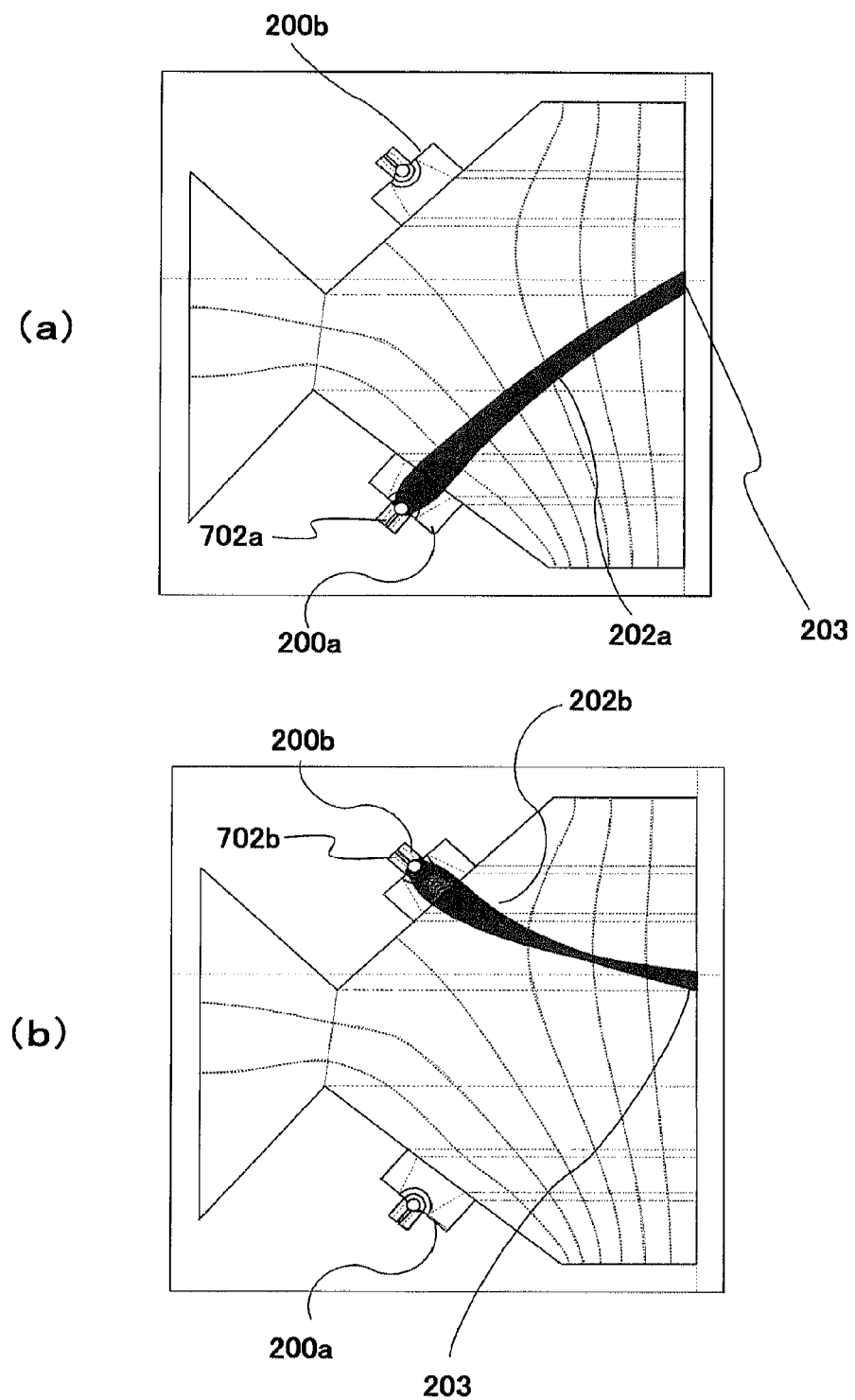
FIG. 8 is a diagram showing an example of an electron beam orbit when an actual focal point is formed on the anode of the X-ray tube used in the first embodiment of the present invention.

FIG. 5 shows an example of the structure of thus-constructed X-ray tube 9, FIG. 6 is an enlarged view of the neighborhood of the cathode 200a, 200b of the X-ray tube 9, FIG. 7 shows an example of the detailed structure of the cathode, and FIG. 8 shows an example of an electron beam orbit when an actual focal point is formed at the position of the focal point 203.

As shown in FIG. 5, the X-ray tube 9 comprises the cathodes 200a and 200b for emitting electron beams, the rotational anode 204 opposed to these cathodes and an outer envelope 701 in which the cathodes 200a and 200b and the rotational anode 204 are vacuum-tightly sealed. As shown in FIG. 6, the cathodes 200a and 200b are disposed so as to be electrically insulated from each other, and the focal points 203 are formed at the same position by adjusting the distance β between the cathode 200a, 200b and the rotational anode 204 and the angle θ of the cathode 200a, 200b opposed to the anode 204.

Furthermore, as shown in FIG. 7, each of the cathodes 200a and 200b comprises a filament 702 for emitting an electron beam (a first filament 702a in the first cathode 200a and a second filament 702b in the second cathode 200b described later), and a focusing member 703 (a focusing member 703a of the cathode 200a and a focusing member 703b of the cathode 200b described later) having a focusing groove portion for focusing the electron beam 202a, 202b from the filament 702 (see FIG. 4), and the filament 702 is disposed so as to be electrically insulated from the focusing member 703 and the grid 201 (the grid 201a corresponding to the cathode 200a, the grid 201b corresponding to the cathode 200b).

When the first grid 201a is opened, the electron beam 220a is emitted from the first filament 702a, and accelerated and focused by potential gradient between the first cathode 200a and the rotational node 204 as shown in FIG. 8(a), so that a actual focal point is formed at the focal point position 203. Likewise, when the second grid 201b is opened, the electron beam 202b is emitted from the second filament 702b, and accelerated and focused by potential gradient between the second cathode 200b and the rotational anode 204, so that a actual focal point is formed at the focal point position 203 as shown in FIG. 8(b).

The opening/closing of the first grid 201a and the second grid 201b is performed by controlling the voltage applied to the electrodes of the grids. When the grid is opened, the voltage between the electrode of the grid and the cathode is set to zero, and when the grid is closed, a negative voltage of several kV is applied between the electrode of the grid and the cathode.

Figure 9:
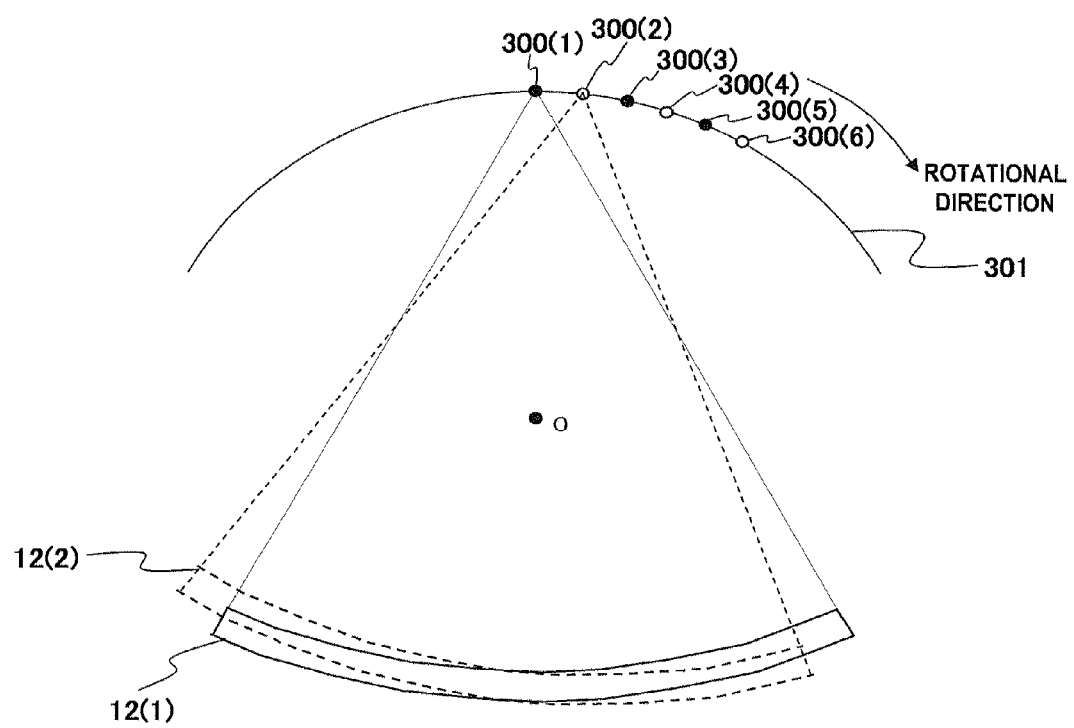
FIG. 9 is a diagram showing the positional relationship between an X-ray focal point position on a scanner rotational plate for collecting projection data and an X-ray detector in the first embodiment of the present invention.

FIG. 9 is a diagram showing the positional relationship between the X-ray detector 12 and the X-ray focal point position 300 on the rotational plate in connection with the rotation of the rotational plate 16 when the high energy X-ray and the low energy X-ray are irradiated while alternately switched with each other every adjacent projection angles, thereby collecting projection data.

In FIG. 9, the position on the rotational plate of the X-ray focal point 203 at each imaging time every projection angle is represented by 300(1), 300(2), 300(3), 300(4), ..., and the position of the X-ray detector 3 at this time is represented by 12(1), 12(2), . . . . O represents the rotational center of the rotational plate 16. In this example, the high energy X-ray is emitted at odd-number positions 300(1), 300(3), 300(5), ... on the rotational plate of the X-ray focal point 203, and the low energy X-ray is emitted at even-number positions 300(2), 300(4), 300(6), . . . . The positions of the X-ray detector 12 corresponding to these X-ray emission positions are represented by odd numbers and even numbers, and they are represented by a solid line and a dashed line.

By the above construction, the high energy X-ray and the low energy X-ray are prevented from being emitted at the same time. When the X-ray focal point 203 is located at the position 300(1) of the rotational plate 16, the examinee 23 is irradiated with the high energy X-ray, and the X-ray transmitted through the examinee is detected by the X-ray detector 12 located at the position of 12(1) represented by the solid line of FIG. 9.

When the rotational plate 16 rotates and thus the X-ray focal point 203 reaches the position 300(2) of the rotational plate 16, the examinee 23 is irradiated with the low energy X-ray, and the X-ray transmitted through the examinee is detected by the X-ray detector 12 located at the position of 12(2) represented by the dash line of FIG. 9.

As described above, the high energy X-ray and the low energy X-ray are alternately irradiated every adjacent projection angles, the X-rays transmitted through the examinee are detected at the positions of the X-ray detector 12 corresponding to the projection angles concerned, the detected data are collected by the data collecting device 15, the collected data are transmitted to the image processing device 21, and a dual energy pickup image is generated in the image processing device 21.

Figure 10:
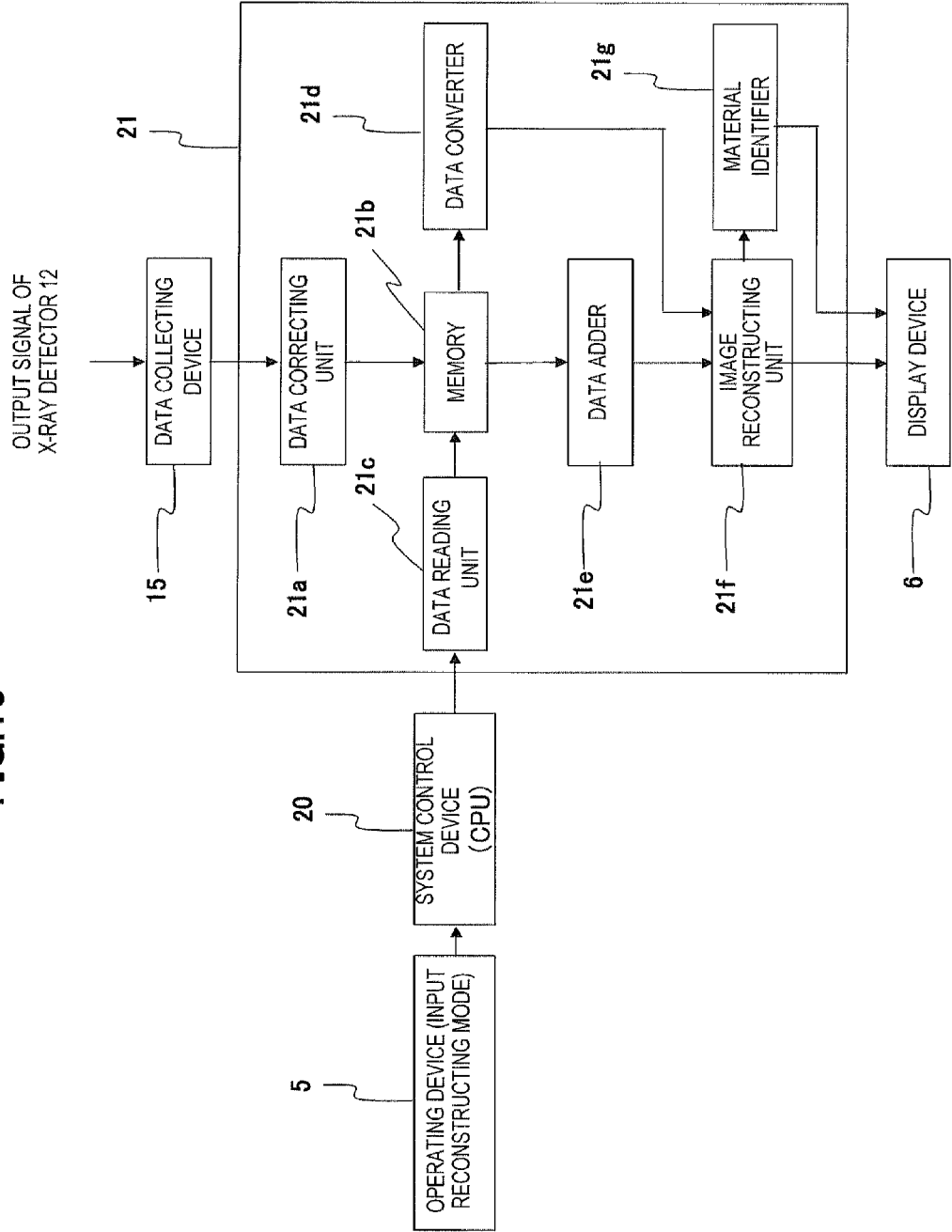
FIG. 10 is a diagram showing the construction of an image processing apparatus of an X-ray CT apparatus to which the present invention is applied.

FIG. 10 is a block diagram showing a part of generating the dual energy pickup image by using the data collected in the data collecting device 15.

In FIG. 10, the image processing device 21 comprises a data correcting unit 21a for correcting (offset correction, gain correction, etc.) the X-ray detection data collected in the data collecting device 15, a memory 21b for storing projection data corrected in the data correcting unit 21a, a data reading unit 21c for reading out projection data based on the high-energy X-ray imaging and projection data based on the low energy X-ray imaging stored in the memory 21b according to a reconstructing mode instruction input to the operation device 5 by the operator, a data adder 21e for adding pairs of adjacent views of the projection data of the high energy X-ray imaging and the projection data of the low energy X-ray imaging (300(1) and 300(2), 300(3) and 300(4), ... in FIG. 3) read out from the memory 21b, an image reconstructing unit 21f for conducting well-known reconstructing calculation such as filtering, back projection, etc. by using the projection data read out from the memory 21b according to the reconstructing mode instruction to thereby reconstruct a CT image of the examinee 23, a data converter 21d for reading out the projection data based on the high energy X-ray imaging and the projection data based on the low energy X-ray imaging in the adjacent views which are stored in the memory 21b, and creating an X-ray attenuation image based on the photoelectric effect (hereinafter referred to as photoelectric effect image) and an X-ray attenuation image based on the Compton scattering (hereinafter referred to as Compton image) by using a well-known method disclosed in the non-patent Document 1, and a material identifier 21g for determining an average atomic number and an average density of the examinee by using the converted data obtained in the data converter 21d on the basis of the CT images of the photoelectric effect image and the Compton image according to the well-known method disclosed in the Non-patent document 1, identifying material for each pixel in the CT image on the basis of the information of the average atomic number and the average density, and outputting the information to the display device 6.

In FIG. 10, the reconstructing mode input to the operation device 5 can be selected from (1) a separate mode in which the projection data based on the high energy X-ray imaging and the projection data based on the low energy X-ray imaging are individually subjected to image reconstruction, (2) an image addition mode in which the data adder 21e is operated, and data obtained by adding (or subtracting) the projection data based on the high energy X-ray imaging and the projection data based on the low energy X-ray imaging as described above is subjected to image reconstruction, and (3) a material identifying mode for identifying material as described elsewhere.

A dedicated processor, a well-known general-purpose processor or the like is applied to the data adder 21e, the image reconstructing unit 21f, the data converter 21d and the material identifier 21g.

Furthermore, it is desired that the number of projection angles at which the high energy X-ray and the low energy X-ray are irradiated, that is, the number of views is larger than that of the normal CT imaging to suppress the radial artifact and discriminate the issues of a human body, and typically it is preferably twice as large as 1024 views under the normal CT imaging, that is, 2048 views.

As described above, in the case of the view number of 2048, when one-rotation time of the rotational plate, that is, one-scan time is set to 0.33 second, the high energy X-ray and the low energy X-ray are alternately applied to the examinee 23 to perform imaging every time the rotational plate 16 rotates at 0.17 [deg], and thus it is required to perform the switching operation between the high energy X-ray and the low energy X-ray at high speed.

Figure 11:
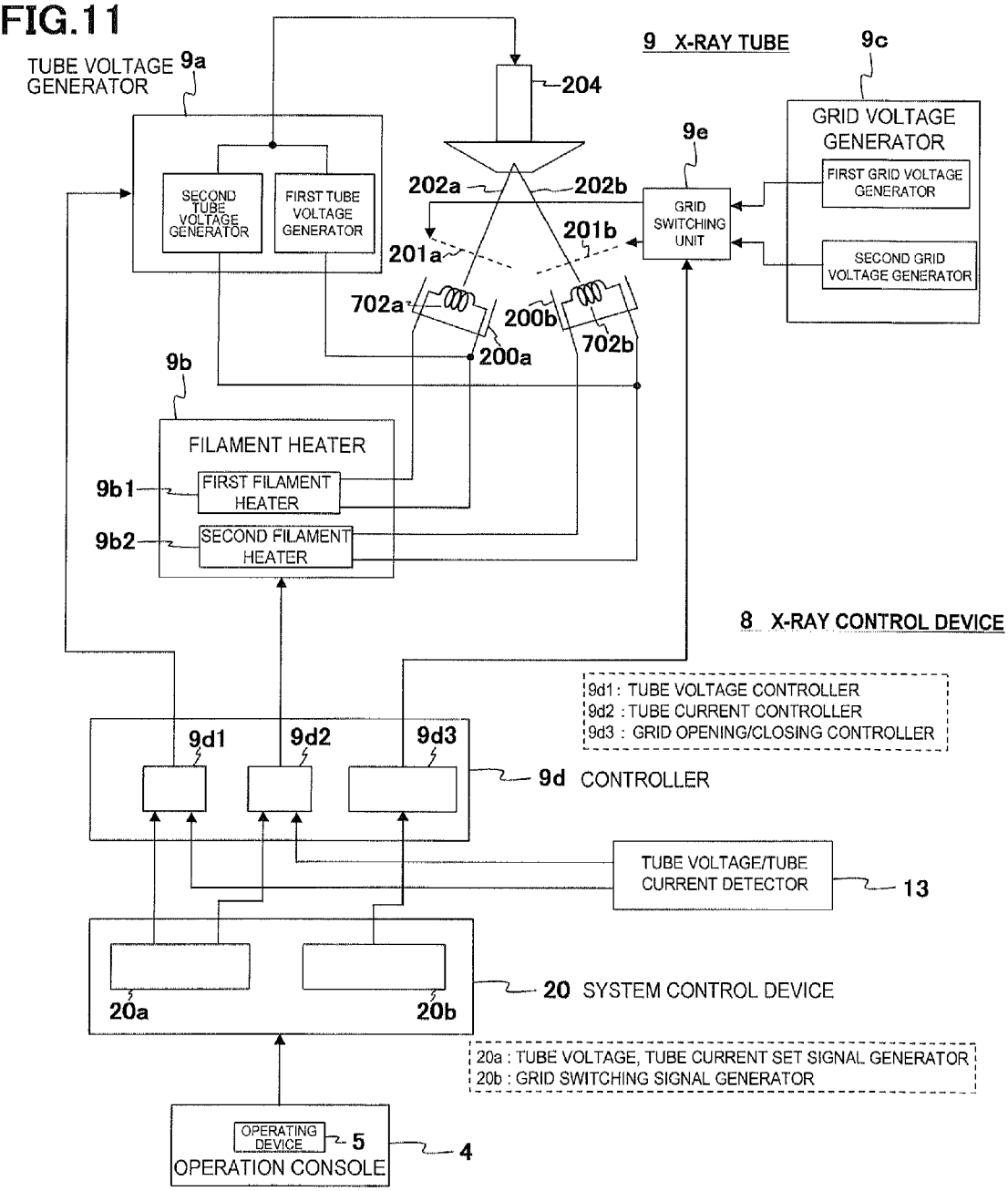
FIG. 11 is a diagram showing the construction of an X-ray control device of the X-ray generating apparatus according to the present invention.

FIG. 11 is an example of a block diagram showing the construction of the X-ray control device 8 (FIG. 2) for performing the dual energy imaging while alternately switching the high energy X-ray and the low energy X-ray from the X-ray tube 9.

The X-ray control device 8 comprises a tube voltage generator 9a for generating a high tube voltage applied between the anode 204 and the first cathode 200a and a low tube voltage applied between the anode 204 and the second cathode 200b, a filament heater 9b for heating the first filament 702a and the second filament 702b so as to obtain the tube current corresponding to the high tube voltage and the low tube voltage, a grid voltage generator 9c (grid voltage generating means) for generating a voltage for opening/closing the first grid 201a and the second grid 201b, a grid switching unit 9e (electron beam emission control means) for switching the first grid 201a and the second grid 201b, and a controller 9d for controlling the tube voltage generator 9a, the filament heater 9b, the grid voltage generator 9c and the grid switching unit 9e.

The controller 9d comprises a tube voltage controller 9d1 for controlling the tube voltage generator 9a to output the high tube voltage and the low tube voltage, a tube current controller 9d2 for controlling the filament current so that the filament current is equal to the tube current set in accordance with the high tube voltage and the low tube voltage, and a grid voltage controller 9d3 for controlling the grid voltage generating unit 9c so that the output voltage of the grid voltage generating unit 9c is equal to zero (open the grid) and a high voltage of about −1000V (close the grid).

When the high tube voltage set value and the low tube voltage set value are set and input from the operation device 5 of the operation console 4 to the system control device (CPU) 20, the tube voltage set signals corresponding to these set values are generated in a tube voltage/tube current set signal generator 20a, and the tube voltage controller 9d1 performs the control so that the generated high tube voltage set signal and low tube voltage set signal are coincident with the actual high tube voltage and low tube voltage of the X-ray tube 9 which are detected by the tube voltage/tube current detecting device 13 (FIG. 2).

Figure 12:
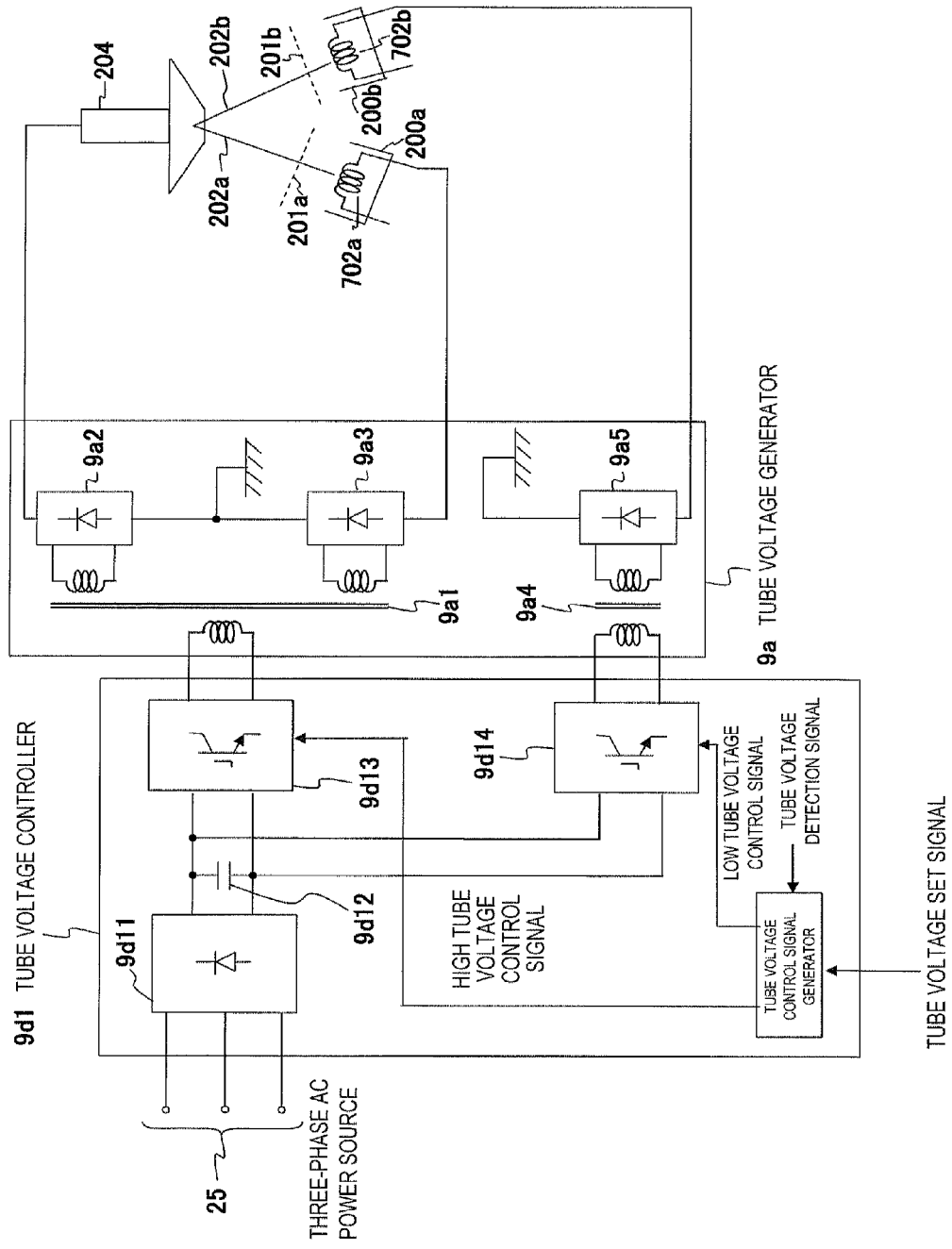
FIG. 12 is a diagram showing the construction of a tube voltage generator and a tube voltage controller in the X-ray control device of the X-ray generating apparatus according to the present invention.

FIG. 12 shows an example of the circuit construction of the tube voltage generator 9a and the tube voltage controller 9d1 (tube voltage control means).

In FIG. 12, the tube voltage controller 9d1 comprises a converter circuit 9d11 for converting an AC voltage of a three-phase AC power source 25 to a DC voltage, a smoothing capacitor for smoothing the output DC voltage (three-phase full-wave rectified voltage) of the converter circuit 9d11, a first inverter circuit 9d13 for converting the DC voltage of the smoothing capacitor 9d12 to an AC voltage having a frequency (for example, 20 kHz or more) which is further higher than the three-phase AC power source frequency and also controlling the high tube voltage, a second inverter circuit 9d14 for converting the DC voltage of the smoothing capacitor 9d12 to an AC voltage having a high frequency (for example, 20 kHz or more) and controlling the low tube voltage, and a tube voltage control signal generator 9d15 for generating the high tube voltage control signal of the first inverter circuit 9d13 and the low tube voltage control signal of the second inverter circuit 9d14. The tube voltage control signal generator 9d15 generates a high tube voltage control signal and a low tube voltage control signal for controlling the operating phases of the first inverter circuit 9d13 and the second inverter circuit 9d14 so that the tube voltage set signal (the high tube voltage set signal and the low tube voltage set signal) generated in the tube voltage/tube current set signal generator 20a (see FIG. 11) of the system control device (CPU) 20 is coincident with the tube voltage detection value detected by the tube voltage/tube current detecting device 13.

The tube voltage generator 9a comprises a high tube voltage generator for generating a high tube voltage and a low tube voltage generator for generating a low tube voltage. The high tube voltage generator has is equipped with a first high voltage transformer 9a1 having two secondary windings for boosting the output voltage of the first inverter circuit 9d13 to the high tube voltage, and high voltage rectifying circuits 9a2 and 9a3 for converting the voltages of the two secondary windings of the first high voltage transformer 9a1 to DC voltages. The high voltage rectifying circuits 9a2 and 9a3 are connected to each other in series, and the connection point thereof is grounded.

On the other hand, the low tube voltage generator has a second high voltage transformer 9a4 for boosting the output voltage of the second inverter circuit 9d14, and a high voltage rectifying circuit 9a5 for rectifying the secondary winding voltage of the second high voltage transformer 9a4 to a DC voltage, and the low tube voltage is generated from the output voltage of the high voltage rectifying circuit 9a2 and the output voltage of the high voltage rectifying circuit 9a5. In this case, the positive DC output terminal of the high voltage rectifying circuit 9a5 is grounded.

The positive DC output terminal of the high voltage rectifying circuit 9a2 is connected to the rotational anode 204 of the X-ray tube 9, the negative DC output terminal of the high voltage rectifying circuit 9a3 is connected to the first cathode 200a of the X-ray tube 9, and the negative DC output terminal of the high voltage rectifying circuit 9a5 is connected to the second cathode 200b of the X-ray tube 9.

For example when the first inverter circuit 9d13 and the second inverter circuit 9d14 are controlled by the thus-constructed tube voltage control means (the first tube voltage control means, the second tube voltage control means) so that the output voltage of the high voltage rectifying circuit 9a2 is equal to 70 kV, the output voltage of the high voltage rectifying circuit 9a3 is equal to −70 kV and the output voltage of the high voltage rectifying circuit 9a5 is equal to −10 kV, the high tube voltage of 140 kV {=70 kV−(−70 kV)} is applied between the anode 204 and the first cathode 200a of the X-ray tube 9 and the low tube voltage of 80 kV {=70 kV−(−10 kV)} is applied between the anode 204 and the second cathode 200b of the X-ray tube 9 because the outer envelope 701 of the X-ray tube 9 is grounded.

In this case, the first filament 702a and the second filament 702b are controlled to be heated by the filament heater 9b so as to obtain the tube current corresponding to the high tube voltage and the low tube voltage.

Figure 13:
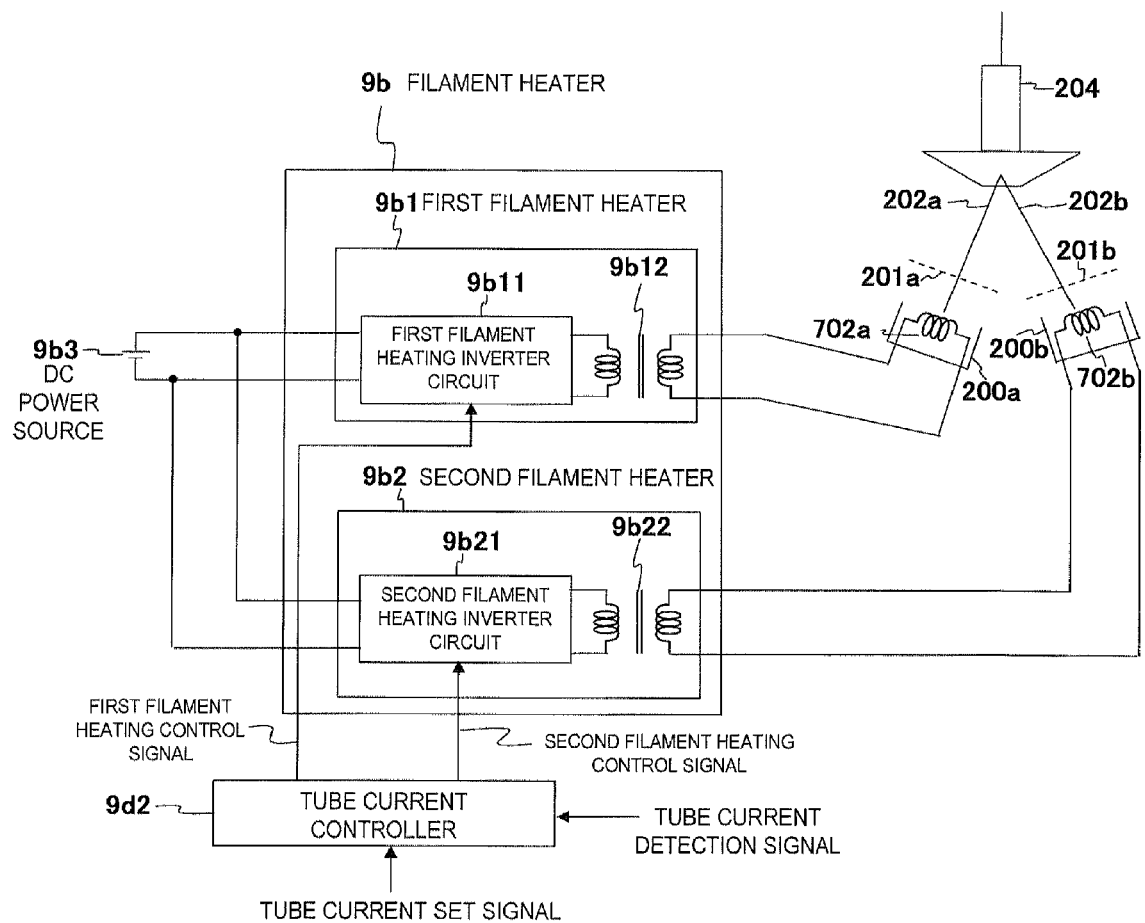
FIG. 13 is a diagram showing the construction of a filament heater and a tube current controller in the X-ray control device of the X-ray generating apparatus according to the present invention.

FIG. 13 shows an example of the circuit construction of the filament heater 9b and the tube current controller 9d2 (tube current control means).

In FIG. 13, the filament heater 9b comprises a first filament heater 9b1 for heating the first filament 702a, a second filament heater 9b2 for heating the second filament 702b and a DC power source 9b3.

The first filament heater 9b1 comprises a first filament heating inverter circuit 9b11 for converting the voltage of the DC power source 9b3 to an AC voltage having a high frequency and also variably controlling the filament current for heating the first filament 702a of the X-ray tube 9, and a first filament heating transformer 9b12 for insulting the output of the first filament heating inverter circuit 9b11 and supplying the output to the first filament 702a. Likewise, the second filament heating circuit 9b2 comprises a second filament heating inverter circuit 9b21 for converting the voltage of the DC power source 9b3 to an AC voltage having a high frequency and also variably controlling the filament current for heating the second filament 702b of the X-ray tube 9, and a second filament heating transformer 9b22 for insulating the output of the second filament heating inverter circuit 9b21 and supplying the output to the second filament 702b.

The tube current controller 9d2 generates a first filament current control signal for controlling the filament current of the first filament 702a corresponding to the low tube current and a second filament current control signal for controlling the filament current of the second filament 702b corresponding to the high tube current, which are used to control the operation phases of the first filament heating inverter circuit 9b11 and the second filament heating inverter circuit 9b21 so that the tube current set signal (the low tube current corresponding to the high tube voltage and the high tube current set signal corresponding to the low tube voltage) generated in the tube voltage/tube current set signal generator 20a of the system control device (CPU) 20 is coincident with the tube current detection value detected by the tube voltage/tube current detecting device 13.

The first filament 702a and the second filament 702b are heated by the filament heater 9b and the tube current controller 9d2 in advance so that preset tube current is obtained (first tube current control means, second tube current control means), the set tube current can be made to flow simultaneously with the opening/closing of the first grids 201a and 201b, so that the problem caused by the thermal inertia of the filament temperature in the prior arts can be solved, and the tube current can be switched at high speed.

Figure 14:
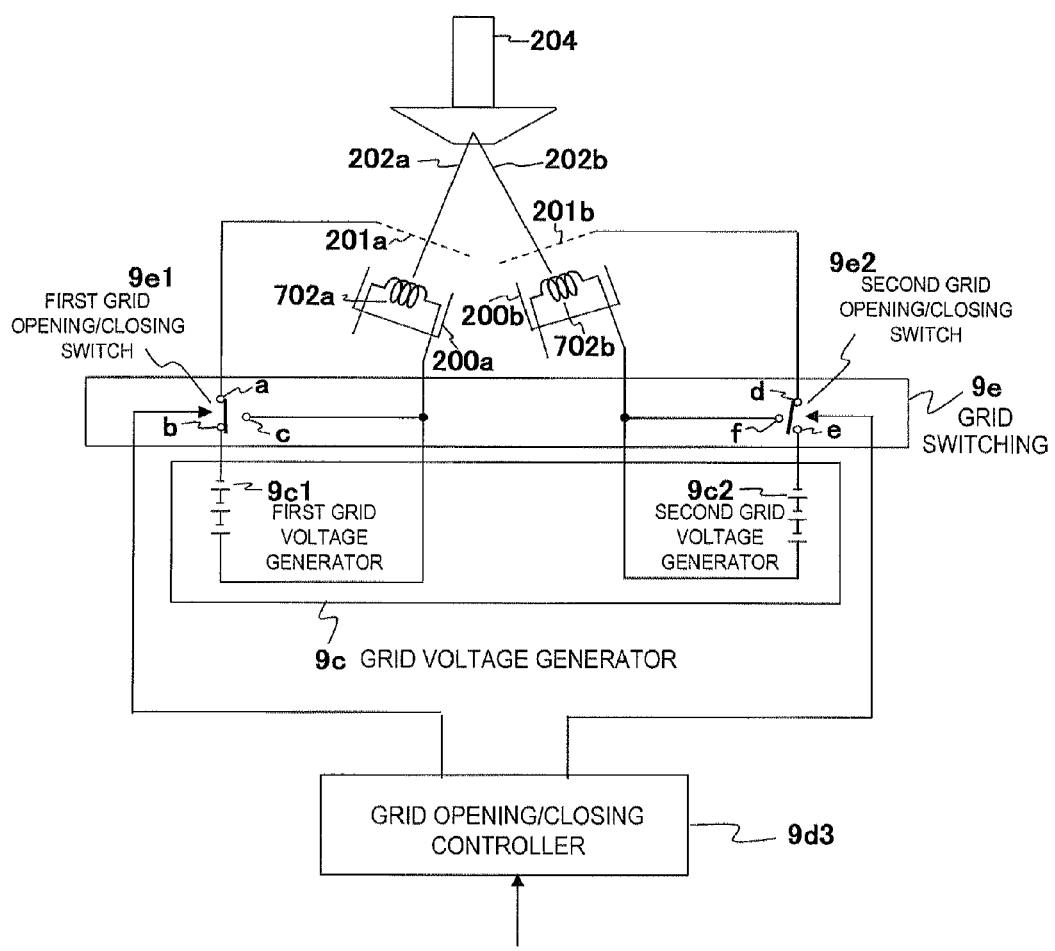
FIG. 14 is a diagram showing the construction of a grid voltage generator and a grid switching unit in the X-ray control device of the X-ray generating apparatus according to the present invention.

FIG. 14 shows an example of the circuit construction of the grid voltage generator 9c and the grid switching unit 9e.

In FIG. 14, the grid voltage generator 9c comprises a first grid voltage generator 9c1 for generating a negative high voltage of about 1000V for closing the first grid 201a of the X-ray tube 9, and a second grid voltage generator 9c2 for generating a negative high voltage of about 1000V for closing the second grid 201b (grid voltage generating means), and the grid switching unit 9e (electron beam emission control means) comprises a first grid opening/closing switch 9e1 for controlling the opening/closing of the first grid 201a, and a second grid opening/closing switch 9e2 for controlling the opening/closing of the second grid 201b.

The grid switching unit 9e is supplied with a grid switching opening/closing signal generated in the grid switching signal generator 20b (see FIG. 11) of the system control device (CPU) 20 through the grid opening/closing controller 9d3 of the controller 9d. When the first grid 201a is opened, the grid switching unit 9e connects a of the first grid opening/closing switch 9e1 to c so that the voltage applied to the first grid 201a is set to zero, and when the first grid 201a is closed, the grid switching unit 9e connects a of the first grid opening/closing switch 9e1 to b so that a negative voltage of about 1000V is applied to the first grid 201a.

Likewise, on the basis of the grid switching opening/closing signal, the grid switching unit 9e connects d of the second grid opening/closing switch 9e2 to f so that the voltage applied to the second grid 201b is set to zero when the second grid 201b is opened, and connects d of the second grid opening/closing switch 9e2 to e so that a negative voltage of about 1000V is applied to the second grid 201b when the second grid 201b is closed.

In order to switch the opening/closing switch at high speed, the first grid opening/closing switch 9e1 and the second grid opening/closing switch 9e2 is implemented by using a semiconductor switch disclosed in "High-speed Pulse See-through System (Takano, others)", Japan Radiation Technique Society Magazine vol. 57, No. 10, FIG. 2 Structure of MOSEFT super-cascade high-voltage semiconductor switching module (October in 2001), or switching control means based on an optical signal disclosed in FIGS. 8 to 11 of JP-A-2003-317996, for example.

By the thus-constructed grid voltage generator 9c and grid switching unit 9e, the first grid 201a and the second grid 201b are alternately switched to each other on the basis of the grid switching signal generated in the grid switching signal generator 20b, whereby the high energy X-ray and the low energy X-ray can be generated on the basis of the electron beam generated from the cathodes corresponding to the first and second grids.

Figure 15:
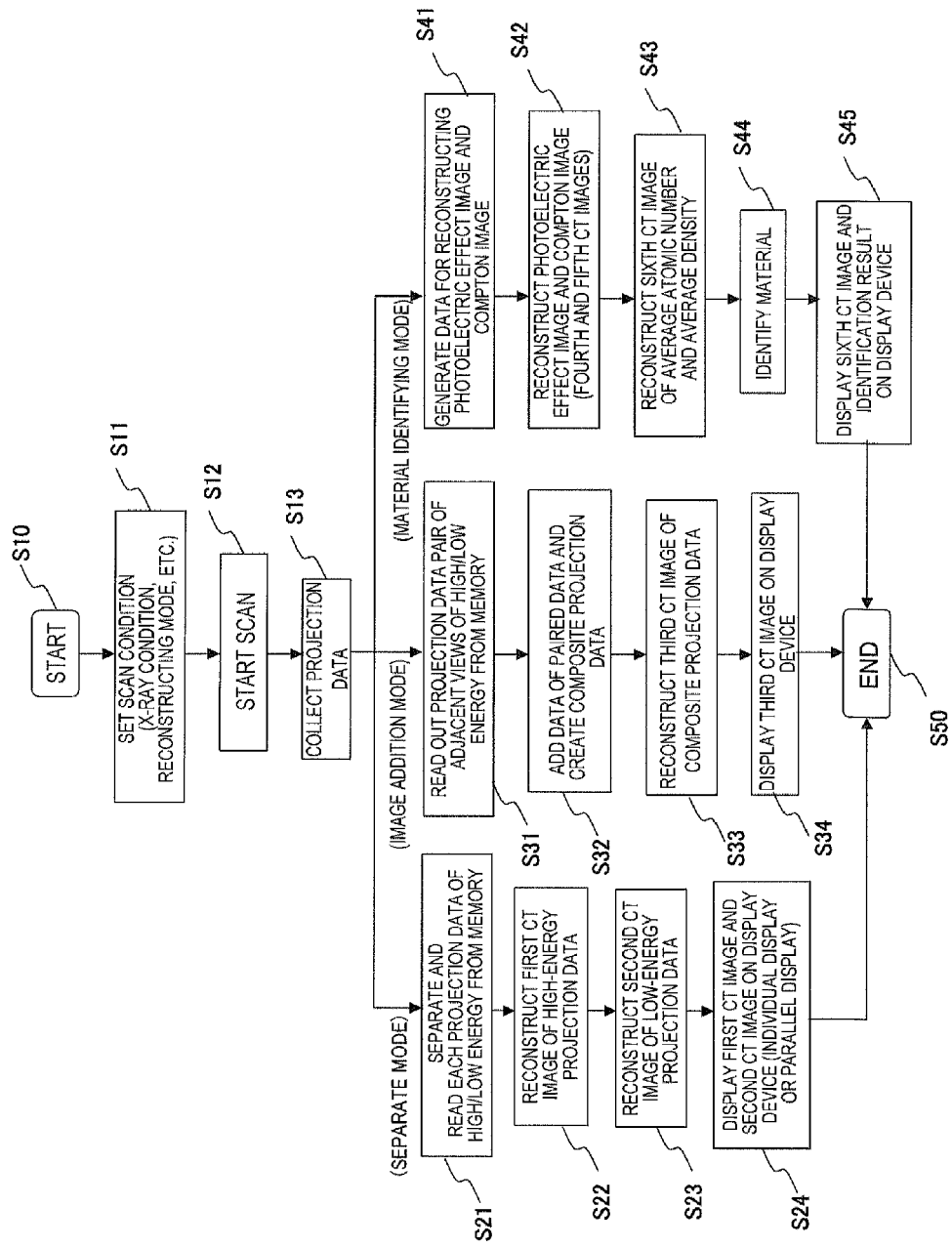
FIG. 15 is a flowchart showing the operation of a material identifying function of the X-ray CT apparatus in the first embodiment of the present invention.

Next, the operation of the thus-constructed X-ray CT apparatus will be described with reference to the flowchart of FIG. 15.

(1) Start (S10)

The operator turns on the power source switch of the operation console 4 to start imaging (multi-energy CT imaging).

(2) Set Scan Conditions (S11)

First, the operator sets scan conditions by using the operating device 5 of the operation console 4 before the imaging.

The main scan conditions contain an X-ray condition A and an X-ray condition B for generating two kinds of X-ray energies to be emitted from the X-ray tube 9, a scan speed (the rotational speed of the rotational plate 16), a slice position of the examinee 23, a slice range, etc, and also a reconstructing mode, etc. as described above.

The X-ray condition contains an X-ray condition A (high energy X-ray) based on a high tube voltage and tube current with which the radiation dosage of the examinee corresponding the high tube voltage is as small as possible, and an X-ray condition B (low energy X-ray) based on a low tube voltage and tube current which is larger than the tube current of the X-ray condition A to the extent that the quantum noise in the pickup image does not increase and thus the image quality of the pickup image is not degraded.

(3) Start Scan (Imaging) (S12)

Subsequently, the operator starts rotation of the rotational plate 16 by operating the operating device 5 of the operation console 4. Driving force from the rotational plate driving device 18 controlled by the rotation control device 17 is transmitted to the rotational plate 16 by the driving force transmission system 19, whereby the rotational plate 16 rotates around the examinee 23. Simultaneously with the start of the rotation of the rotational plate 16, the tube voltages corresponding to the X-ray conditions A and B are respectively applied between the rotational anode 204 and the first cathode 200a of the X-ray tube 1 and between the rotational anode 204 and the second cathode 200b of the X-ray tube 1, and also the filaments 702a and 702b are heated so that the temperatures of the filaments 702a and 702b are equal to the filament temperatures corresponding to the tube current of the X-ray conditions A and B. In order to prevent electron beams from being emitted from these filaments, the first grid 201a and the second grid 201b are electrically closed.

Then, at the time point when the rotational speed of the rotational plate 16 reaches the set scan speed (for example, the rotational speed corresponding to one rotation/0.33 second), the first grid 201a is opened to irradiate the examinee 23 with the X-ray of the X-ray condition A, thereby starting the imaging.

(4) Collect Projection Data (S13)

When the imaging is started, the system control device (CPU) 20 alternately opens/closes the first grid 201a and the second grid 201b every projection angle of the rotational plate 16 corresponding to each of the first grid 201a and the second grid 201b (every 0.17[degree] when the number of views is set to 2048 and the one-scan time is set to 0.33 second, for example) Accordingly, the X-ray based on the X-ray condition A and the X-ray based on the X-ray condition B are alternately applied to the examinee 23.

The X-ray transmitted through the examinee 23 in this imaging operation is detected by the X-ray detector 12, successively collected as projection data in the data collecting device 15, and then transmitted to the image processing device 21.

The data transmitted to the image processing device 21 are subjected to various kinds of correction processing in the data correcting unit 21a, and then these projection data are successively recorded in the memory 21b.

The system control device (CPU) 20 performs the processing of S21 to S24, the processing of S31 to S34 or the processing of S41 to S45 according to the reconstructing mode which is input and set to the operation console 4 by the operator in S11, the image reconstruction and the display of the processing result on the display device 6.

(5) When the Separate Mode is Selected

When the separate mode is selected in S11, the system control device (CPU) 20 executes each of the following steps S21 to S24.

(5-1) Separate and Read Out Projection Data (S21)

When this mode is selected, the system control device (CPU) 20 instructs the data reading unit 21c to read out the projection data of the high energy X-ray imaging views 300(1), 300(3), 300(5), . . . and the projection data of the low energy X-ray imaging views 300(2), 300(4), 300(6), . . . as individual pairs from the memory 21b. Accordingly, the projection data (scan data) based on the high energy X-ray imaging and the projection data (scan data) based on the low energy X-ray imaging data are successively transmitted to the image reconstructing unit 21f.

(5-2) Reconstruct Image (S22, S23)

The image reconstructing unit 21f successively executes the image reconstruction on the projection data of the high energy X-ray imaging successively supplied from the memory 21b and the image reconstruction on the projection data of the low energy X-ray imaging, and creates two CT images (a first CT image and a second CT image). These CT images are stored into the storage device 22 in the console device 4.

(5-3) Display Image (S24)

The two reconstructed CT images are displayed on the screen of the display device 6, and supplied for doctor's image diagnosis. A system of selectively displaying two images or arranging two images in parallel on the screen may be applied as an image display style. Such a technique is well known in this technical field, and thus the description thereof is omitted.

According to the separate mode described above, an internal organ or tissue in the examinee can be imaged according to the X-ray absorption characteristic. Furthermore, the two CT images thus obtained are in the same time phase, and thus the diagnosis based on the multi-energy CT image of a moving internal organ can be performed in a short time and with less exposure.

(6) When the Image Addition Mode is Selected

When the image addition mode is selected in S11, the system controller (CPU) 20 executes each of the following steps S31 to S34.

(6-1) Read Out Projection Data (S31)

When this mode is selected, the system controller (CPU) 20 instructs the data reading unit 21c to successively read out the data from the memory 21b while the high energy X-ray imaging view and the low energy X-ray imaging view which are adjacent to each other are paired like a pair of 300(1) and 300(2), a pair of 300(3) and 300(4), a pair of 300(5) and 300(6), . . . . Accordingly, the pairs of the projection data are successively transmitted to the data adder 21e.

(6-2) Create Composite Projection Data (S32)

The data adder 21e executes addition processing (any one of simple addition, addition average and subtraction) on the paired data of the transmitted projection data to create composite projection data. The number of views of the composite projection data is set to the half of the total views of the number of the high energy X-ray imaging views and the number of the low energy X-ray imaging views, and these data are transmitted to the image reconstructing unit 21f.

(6-3) Reconstruct Image (S33)

The image reconstructing unit 21f executes the reconstructing calculation on the basis of the composite projection data transmitted from the data adder 21e to crate an CT image (third CT image). The thus-created third CT image is stored into the storage device 22 in the console device 4.

(6-4) Display Image (S34)

The reconstructed third CT image is displayed on the screen of the display device 6, and supplied for doctor's image diagnosis.

According to the image addition mode described above, there can be obtained an image having compensated contrast resolution which is short when the examinee is imaged by only one of the high energy X-ray imaging and the low energy X-ray imaging.

The image addition mode can be also implemented by subjecting the two CT image obtained in the separate mode to addition processing, addition averaging processing or the subtraction processing.

(7) When the Material Identifying Mode is Selected

When the material identifying mode is selected in S11, the system controller (CPU) 20 executes each of the following steps S41 to S45.

(7-1) Generate Data for Reconstructing Photoelectric Effect Image and Compton Image (S41)

When this mode is selected, the system controller (CPU) 20 reads out the projection data picked up by the high energy X-ray and the projection data picked up by the low energy X-ray at two adjacent views which are recorded in the memory 21b, and creates, in the data converter 21d, data for reconstructing a photoelectric effect image based on the photoelectric effect and a Compton image based on Compton scattering by using the well-known method disclosed in the non-patent document 1.

(7-2) Reconstruct Photoelectric Effect Image and Compton Image (S42)

Respective CT images of the photoelectric effect image and the Compton image are reconstructed in the image reconstructing unit 21f by using the reconstructing data of the photoelectric effect image and the Compton image which are generated in the data converter 21d (fourth CT image and fifth CT image).

(7-3) Reconstruct CT Image Having Average Atomic Number and Average Density (S43)

ON the basis of the reconstructed CT images of the photoelectric effect image and the Compton image, a CT image (sixth CT image) having an average atomic number and an average density of the examinee 23 is reconstructed in the reconstructing device 21f by using the well-known method disclosed in the non-patent document 1.

(7-4) Identify Material (S44)

The material identification is performed on the basis of the reconstructed sixth CT image of the average atomic number and the average density in the material identifier 21g (material identifying means) by applying a well-known method to each pixel.

(7-5) Display Identification Result (S45)

The identification result obtained in S44 is displayed on the screen of the display device 6. As a display style of the identification result, window information provided with hue information which is different every tissue or material is displayed, and also the hues corresponding to the window information are provided to sites which are different in tissue, material in the sixth CT image.

In this case, by changing the color every material, plural identification results can be displayed at the same time. Typical examples of the materials to be identified contain bone tissue, lung tissue, muscle and fat of a human body, contrast material, etc.

(8) Finish (S50)

When the processing of each mode is finished, the operator turns off the power source switch of the console device 4. At the same time when the imaging (scan) of the indicated imaging range is finished, the system control device (CPU) 20 instructs the X-ray control device 8 and the rotational plate control device to finish the imaging, thereby finishing he radiation of X-ray from the X-ray tube 1 and stopping the rotation of the rotational plate 16.

Furthermore, the above imaging operation and the respective kinds of processing (the image reconstruction processing, the addition processing, the data creation processing of the photoelectric effect image and the Compton image, the material identification processing) are executed in parallel to one another, and the results are successively displayed on the display device 6.

As described above, according to the first embodiment, there is provided the X-ray generating apparatus that controls the voltages to be applied to the grid electrodes and switches the high energy X-ray and the low energy X-ray to each other at high speed by using the X-ray tube having the two cathodes, the anode for forming one X-ray focal point by electron beams emitted from the filaments of the two cathodes and the two grid electrodes corresponding to the two cathodes for controlling emission of the plural electron beams. By the X-ray generating apparatus, the high energy X-ray and the low energy X-ray are irradiated while alternately switched to each other every adjacent views, thereby obtaining the projection data. Therefore, the number of views can be set to the double of the number of views under the normal CT imaging, and also no radial artifact occurs, so that the image quality of the image can be enhanced, and the tissues of the human body can be clearly discriminated from one another.

In this case, the number of views are set to the double of that under the normal CT imaging, and thus the image quality of the CT image can be set to the same level as the prior arts.

Furthermore, when the high energy X-ray based on the high tube voltage is generated, the X-ray is generated while the tube current is reduced from the viewpoint of reducing the exposure, and when the low energy X-ray based on the low tube voltage is generated, the X-ray is generated while the tube current is increased to the extent that the quantum noise in the image does not increase. Therefore, the enhancement of the image quality and the reduction of the exposure can be attained.

Furthermore, the first tube voltage control means and the second tube voltage control means can independently control the high tube voltage and the low tube voltage respectively, and thus the dual energy imaging based on the combination of any high energy X-ray and low energy X-ray can be performed.

<<Second Embodiment>>

Figure 16:
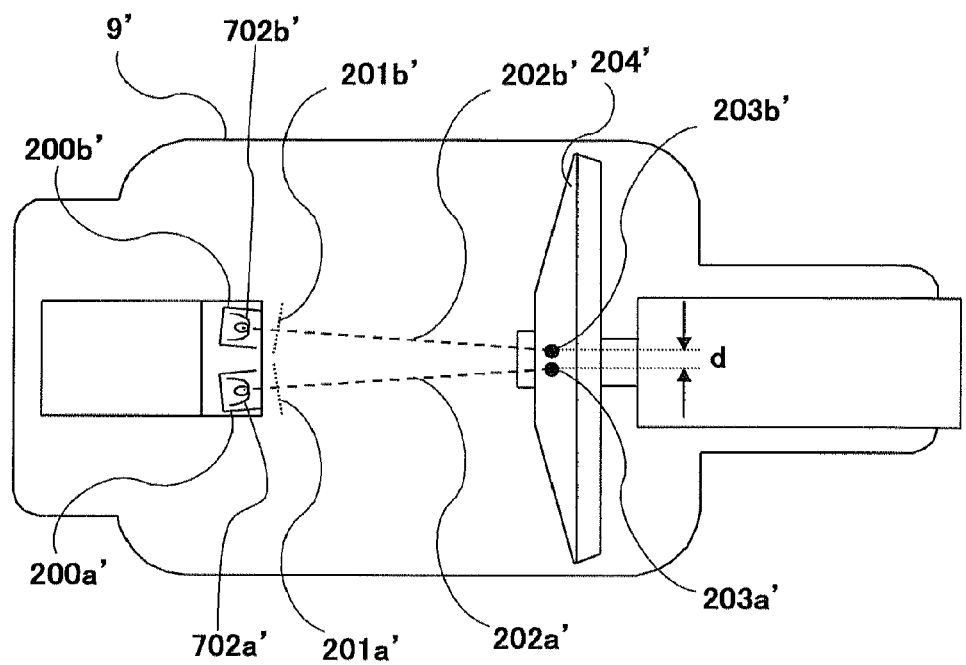
FIG. 16 is a diagram showing the construction of an X-ray tube used in a second embodiment of the present invention.

According to a second embodiment of the present invention, the dual energy imaging is performed by using an X-ray tube 9' shown in FIG. 16.

In FIG. 16, the X-ray tube 9' has a first anode 200a' for generating an electron beam 202a' for generating high energy X-ray, a second cathode 200b' for generating an electron beam 202b' for generating low energy X-ray, a first grid 201a' corresponding to the first cathode 200a' and a second grid 201b' corresponding to the second cathode 200b' for alternately switching the electron beam 202a' and the electron beam 202b' to each other, and a rotational anode 204' for forming two focal points of a first X-ray focal point 203a' and a second X-ray focal point 203b' by focusing the electron beams 202a' and 202b' emitted from the cathodes 200a' and 200b'. The first focal point 203a' and the second focal point 203b' are formed so as to be spaced from each other at a distance of d by adjusting the distance between the cathode 200a', 200b' and the rotational anode 204' and the angles of the cathodes 200a' and 200b' with respect to the rotational anode 204'.

702a' represents a first filament for generating the electron beam 202a', and 702b' represents a second filament for generating the electron beam 202b'.

The thus-constructed X-ray tube 9' is different in only the distance between the cathode 200a', 200b' and the rotational anode 204' and the angles of the cathodes 200a' and 200b' with respect to the rotational anode 204' to form the first and second two focal points 203a' and 203b', and the structure of the X-ray tube 9', the enlarged view of the neighborhood of the cathodes 200a' and 200b' of the X-ray tube 9', the detailed structure of the cathodes and the electron orbit when the actual focal points are formed at the positions of the focal points 203a' and 203b' are substantially the same as FIGS. 5, 6, 7 and 8 of the first embodiment, and thus the description thereof is omitted.

Figure 17:
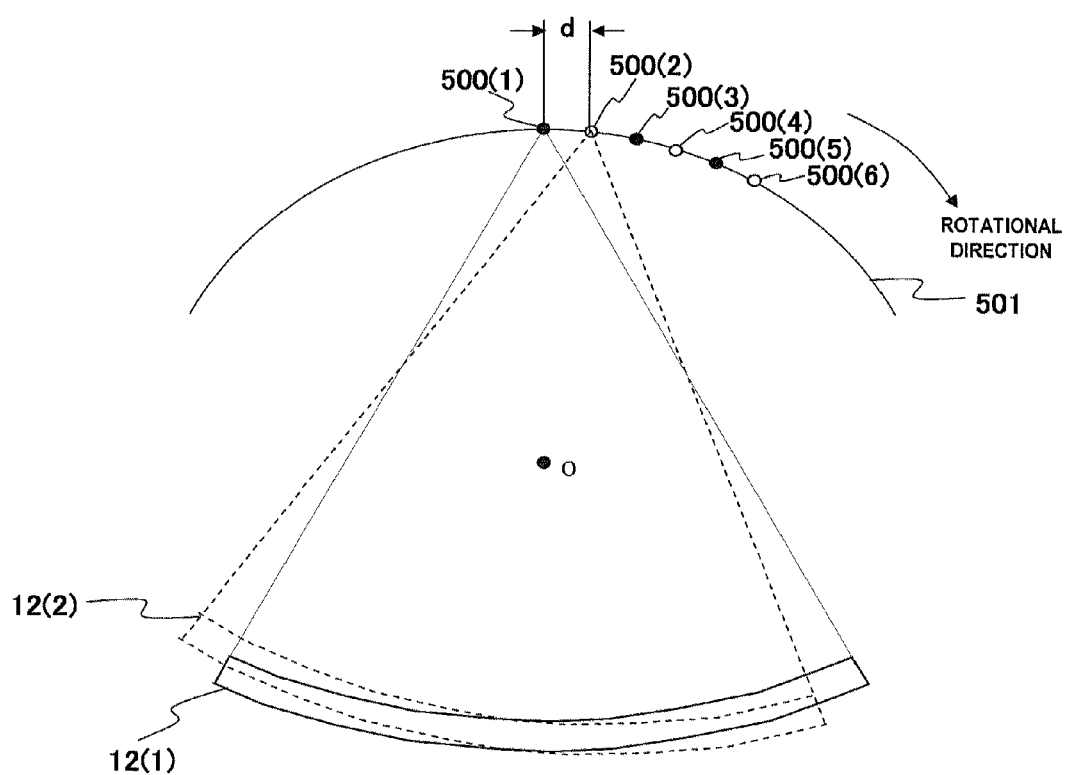
FIG. 17 is a diagram showing the positional relationship between an X-ray focal position on a scanner rotational plate for collecting projection data and an X-ray detector in the second embodiment of the present invention.

FIG. 17 is a diagram showing the positional relationship between the X-ray detector 12 and the X-ray focal point on the rotational orbit in connection with the rotation of the rotational plate 16 when the high energy X-ray and the low energy X-ray are irradiated from the two focal points 203a' and 203b' of the X-ray tube 9' by using the X-ray tube 9' of FIG. 16 while alternately switched to each other every adjacent projection angles, thereby collecting projection data.

In FIG. 17, the position on the rotational orbit of the first X-ray focal point 203a' in each imaging operation at each projection angle is represented by 500(1), 500(3), 500(5), . . . , and the position of the X-ray detector 12 at this time is represented by 12(1), 12(3), . . . .

The position on the rotational orbit of the second X-ray focal point 203b' is represented by 500(2), 500(4), 500(6), . . . , and the position of the X-ray detector 12 is represented by 12(2), 12(4), . . . . In FIG. 16, only 12(1) and 12(2) are shown, and these are represented by a solid line and a dashed line.

In the second embodiment, the high energy X-ray is emitted from the first X-ray focal point 203a' at the odd-number positions 500(1), 500(3), 500(5), . . . on the rotational orbit, the rotational plate 16 rotates and the low energy X-ray is emitted from the X-ray focal point 203b' spaced from the first X-ray focal point 203a' at a distance d at even-number positions 500(2), 500(4), 500(6), . . . . Corresponding to 500(1)+d, 500(3)+d, 500(5)+d, . . . on the rotational plate 16. The transmitted X-ray of the examinee is detected at the positions 12(1), 12(2), . . . . Of the X-ray detector 12 which correspond to the above X-ray emission positions.

As in the case of the first embodiment, the high energy X-ray and the low energy X-ray are emitted every adjacent projection angles, the X-ray transmitted through the examinee is detected at the position of the X-ray detector 12 corresponding to the projection angle concerned, and the detected data are collected in the data collecting device 15 and transmitted to the image processing device 21 to generate a dual energy pickup image in the image processing device.

By the above construction, the same effect as the first embodiment can be obtained, and the X-ray can be surely emitted from the second focal point 203b' at the position spaced at the distance d. Therefore, thereby preventing reduction of the resolution which is concerned to occur due to the positional displacement between the position of 500(2), 500(4), 500(6), . . . and the X-ray focal point position.

<<Third Embodiment>>

Figure 18:
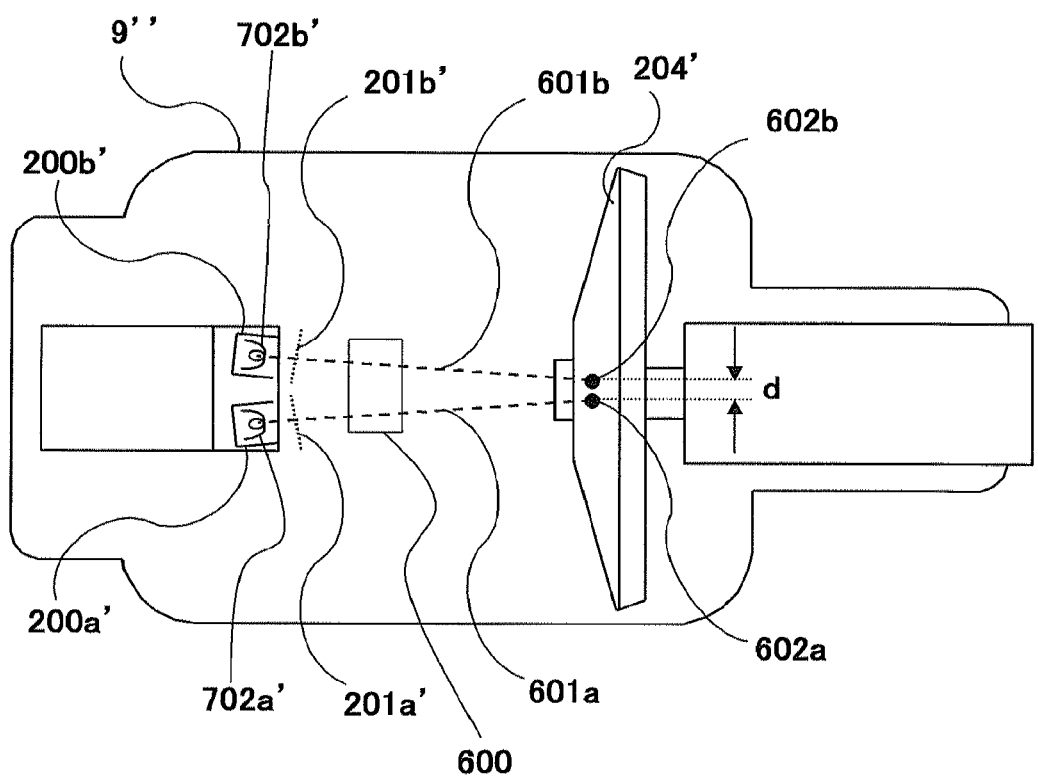
FIG. 18 is a diagram showing the construction of an X-ray tube used in a third embodiment of the present invention.

A third embodiment of the present invention performs the dual energy imaging by using an X-ray pipe 9''' shown in FIG. 18.

The difference from the X-ray pipe 9' of the second embodiment resides in that electron beam deflecting means comprising a deflection coil 600 for deflecting the direction of an electron beam emitted from the cathode and a magnetic field generating current supply source (deflection current supply means) (not shown) for making current flow through the coil to generate magnetic field.

In FIG. 18, the X-ray tube 9' has a first cathode 200a' for generating an electron beam 601a for generating high energy X-ray, a second cathode 200b' for generating an electron beam 601b for generating low energy X-ray, a first grid 201a' corresponding to the first cathode 200a' and a second grid 201b' corresponding to the second cathode 200b' for alternately switching the electron beam 601a and the electron beam 601b to each other, a deflection coil 600 for changing the travel directions of the electron beams 601a, 601b, and a rotational anode 204' for focusing the electron beams 601a and 601b emitted from the cathodes 200a' and 200b' and forming two focal points 602a and 602b of the first X-ray focal point 602a and the second X-ray focal point 602b.

702a' represents a first filament for generating the electron beam 202a', and 702b' represents a second filament for generating the electron beam 202b'.

The deflection coil 600 can generate magnetic field in the vertical direction of the sheet plane, and control the intensity of the magnetic field to adjust the travel directions of the electron beams 601a, 601b in the up-and-down direction of the sheet plane. Particularly by applying the magnetic field to the electron beam 601a and the electron beam 601b in the opposite directions respectively, the travel directions of the respective electron beams can be changed to the opposite directions to each other. That is, by adjusting the intensity of the magnetic field and the applying direction of the magnetic field, the positions of the first X-ray focal point 602a and the second X-ray focal point 602b which are formed by the electron beams 601a and 601b, and the distance between these focal points can be arbitrarily adjusted.

Of course, it is possible to set the distance d to zero so that the focal point position is single.

It is more preferable that the distance d between the focal points is changed in accordance with the scan speed. Accordingly, in such a case, for example, the distance d may be variably controlled by the electron beam deflecting means so that the distance d is increased when the scan speed is high.

As in the case of the first embodiment, the high energy X-ray and the low energy X-ray are emitted every projection angle, the X-ray transmitted through the examinee is detected at the positions of the X-ray detector 12 corresponding to the projection angles, the detected data are collected by the data collecting device 15, and the collected data are transmitted to the image processing device 21 to generate a dual energy pickup image in the image processing device.

In the dual energy X-ray imaging using the thus-constructed X-ray tube 9''', the same effect as the first embodiment and the second embodiment can be obtained. In addition, as shown in FIG. 17, the distance d of the focal point position which is required to be shifted on an arc 501 is varied in accordance with the projection number per rotation, however, there is an advantage that the focal point position can be varied in accordance with various projection numbers by using the X-ray tube 9''' shown in FIG. 18.

The first to third embodiments in which the dual energy imaging is performed by alternately switching the high energy X-ray and the low energy X-ray to each other every adjacent views by using the X-ray generating apparatus for switching the high energy X-ray and the low energy X-ray has been described. However, the present invention is not limited to the dual energy imaging, and the present invention may be applied to multi-energy based on three or more X-ray energies.

The following X-ray generating apparatuses of (1), (2) and (3) are applied under the multi-energy imaging.

(1) An X-ray generating apparatus comprising an X-ray tube having an anode for forming one focal point by electron beams from three or more plural cathodes and plural grids corresponding to the cathodes for switching the electron beams from the plural cathodes, and plural X-ray energy control means for controlling plural X-ray energies generated from the X-ray tube.

(2) An X-ray generating apparatus comprising an X-ray tube having an anode for forming three or more X-ray focal points by electron beams from three or more plural cathodes, and plural grids corresponding to the cathodes for switching the electron beams from the plural cathodes, and plural X-ray energy control means for controlling plural X-ray energies generated from the X-ray tube.

(3) An X-ray generating apparatus an X-ray tube which is obtained by providing the X-ray tube of (2) with electron beam deflecting means for deflecting the direction of the electron beam and deflects the direction of the electron beam by the electro beam deflecting means to form plural X-ray focal points, and plural X-ray energy control means for controlling plural X-ray energies generated from the X-ray tube.

In the above embodiments, the high energy X-ray and the low energy X-ray are switched every adjacent views to perform the dual energy imaging by one scan. However, subsequently to the above scan, the imaging based on X-ray energy different from that of the previous scan may be performed on the same slice position.

The X-ray generating apparatus according to this invention and the X-ray CT apparatus using the X-ray generating apparatus are applied to a human body as a target. However, the present invention is not limited to the human body, but applicable to a baggage scanner for detecting existence of detonating powder, that is, explosive material in baggage.

The invention claimed is:

1. An X-ray generating apparatus including
   an X-ray tube for emitting X-ray,
   tube voltage control means configured to control a tube voltage,
   tube current control means configured to control tube current of the X-ray tube, and
   X-ray control means configured to control high-energy X-ray and low-energy X-ray by the tube voltage control means, wherein
   the X-ray tube includes
      plural cathodes each of which has a filament,
      one anode opposed to the plural cathodes,
      grid electrodes each of which is individually provided to every cathode to control discharge of an electron beam emitted from the cathode,
      grid voltage generating means configured to generate a voltage to be applied to each grid electrode, and
      electron beam emission control means configured to alternately apply the grid voltage generated in the grid voltage generating means to each of the grid electrodes to control the emission of the electron beam, and wherein
   the tube voltage control means includes
      first tube voltage control means configured to control a high tube voltage corresponding to the high energy X-ray, and
      second tube voltage control means configured to control a low tube voltage corresponding to the low energy X-ray, and wherein
   the tube current control means includes
      first tube current control means configured to control tube current corresponding to the high energy X-ray, and
      second tube current control means configured to control tube current corresponding to the low energy X-ray.

2. The X-ray generating apparatus according to claim 1, wherein the X-ray tube is an X-ray tube for emitting plural electron beams from the plural filaments and forming plural X-ray focal points on the anode so that the X-ray focal points are spaced from one another at a predetermined distance on the anode.

3. The X-ray generating apparatus according to claim 1, wherein the X-ray tube further comprises electron beam deflecting means for deflecting the directions of the electron beams generated from the plural filaments.

4. The X-ray generating apparatus according to claim 3, wherein the electron beam deflecting means has a deflection coil provided between the anode and the plural cathodes and deflection current supply means for supplying the deflection coil with current for deflecting the directions of the electron beams.

5. The X-ray generating apparatus according to claim 1, wherein the tube current controlled by the second tube current control means is larger than the tube current controlled by the first tube current control means.

6. An X-ray CT apparatus that has a multi-energy imaging function, the X-ray CT apparatus comprising
   an X-ray tube configured to irradiate X-ray to an examinee,
   an X-ray detector configured to detect X-ray transmitted through the examinee,
   scanner rotating means rotating around the examinee while the X-ray tube and the X-ray detector are mounted therein,
   X-ray control means configured to irradiate X-rays having plural different energies emitted from the X-ray tube to the same slice position of the examinee while switching the X-rays every projection angle, and
   image reconstructing means configured to reconstruct projection data detected by the X-ray detector to obtain a CT image, wherein
   the X-ray tube comprises
      plural cathodes each of which has a filament,
      one anode opposed to the plural cathodes, and
      grid electrodes each of which is individually provided every cathode to control emission of an electron beam emitted from the cathode, wherein
   the X-ray control means comprises
      tube current control means configured to heat the cathode filaments of the X-ray tube and control the tube current flowing between the anode and the cathodes,
      tube voltage control means configured to control a tube voltage to be applied between the anode and the cathodes,
      grid voltage generating means configured to generate a voltage to be applied to each grid electrode, and
      electron beam emission control means configured to apply the grid voltages generated in the grid voltage generating means to the respective grid electrodes while alternately switching the grid voltages at every projection angle, thereby controlling emission of the electron beams, wherein
   the tube voltage control means comprises
      first tube voltage control means configured to control a high tube voltage corresponding to the high energy X-ray, and
      second tube voltage control means configured to control a low tube voltage corresponding to the low energy X-ray, and wherein
   the tube current control means comprises
      first tube current control means configured to control tube current corresponding to the high energy X-ray, and
      second tube current control means configured to control tube current corresponding to the low energy X-ray.

7. The X-ray CT apparatus according to claim 6, wherein the X-ray tube is an X-ray tube for emitting plural electron beams from the plural filaments and forming plural X-ray focal points on the anode so that the X-ray focal points are spaced from one another at a predetermined distance on the anode.

8. The X-ray CT apparatus according to claim 6, wherein the X-ray tube further comprises electron beam deflecting means for deflecting the directions of the electron beams generated from the plural filaments.

9. The X-ray CT apparatus according to claim 8, wherein the electron beam deflecting means has a deflection coil provided between the anode and the plural cathodes and deflection current supply means for supplying the deflection coil with current for deflecting the directions of the electron beams.

10. The X-ray CT apparatus according to claim 6, wherein the tube current controlled by the second tube current control means is larger than the tube current controlled by the first tube current control means.

11. The X-ray CT apparatus according to claim 6, wherein the number of projection angles for detecting the projection data is larger than that under CT imaging using single X-ray energy.

12. The X-ray generating apparatus according to claim 1, wherein the X-ray tube emits high energy X-ray and low energy X-ray alternately at each projection angle, under control of the X-ray control means, to perform dual energy imaging, by alternately apply the grid voltage to each of the grid electrodes at said each projection angle.

13. The X-ray generating apparatus according to claim 1, wherein the tube voltage control means causes a high tube voltage to be applied between the anode and a first cathode of the plural cathodes, and causes a low tube voltage to be applied between the anode and a second cathode of the plural cathodes.

14. An X-ray generating apparatus comprising:
an X-ray tube configured to emit X-ray; and
an X-ray control part configured to control tube voltage and tube current of the X-ray tube, and to control the X-ray tube to emit high-energy X-ray and low-energy X-ray, wherein
the X-ray tube includes
    plural cathodes each of which has a filament,
    an anode opposed to the plural cathodes,
    grid electrodes each of which is individually provided to every cathode to control discharge of an electron beam emitted from the cathode,
    grid voltage generating part configured to generate a grid voltage to be applied to each grid electrode, and
    electron beam emission control part configured to alternately apply the grid voltage to each of the grid electrodes to control the emission of the electron beam, and wherein
the X-ray control part comprises
    first tube voltage control means configured to control a high tube voltage corresponding to the high energy X-ray,
    second tube voltage control means configured to control a low tube voltage corresponding to the low energy X-ray,
    first tube current control means configured to control tube current corresponding to the high energy X-ray, and
    second tube current control means configured to control tube current corresponding to the low energy X-ray.

* * * * *